US006939846B2

(12) United States Patent
Lipton et al.

(10) Patent No.: US 6,939,846 B2
(45) Date of Patent: Sep. 6, 2005

(54) USE OF A POLYPEPTIDE FOR TREATMENT OF PRURITIS IN ANIMALS

(75) Inventors: James M. Lipton, Woodland Hills, CA (US); Anna P. Catania, Milan (IT)

(73) Assignee: Zengen, Inc., Woodland Hills, CA (US)

( * ) Notice: Subject to any disclaimer, the term of this patent is extended or adjusted under 35 U.S.C. 154(b) by 253 days.

(21) Appl. No.: 10/023,287

(22) Filed: Dec. 17, 2001

(65) Prior Publication Data

US 2003/0129156 A1 Jul. 10, 2003

(51) Int. Cl.$^7$ .......................... C12Q 1/68; A61K 38/10; A61K 7/06

(52) U.S. Cl. .............................. 514/2; 424/70.14; 435/6

(58) Field of Search .......................... 424/70.14; 514/12, 514/2; 435/6; 530/300, 350

(56) References Cited

U.S. PATENT DOCUMENTS

| | | | |
|---|---|---|---|
| 5,028,592 A | 7/1991 | Lipton | |
| 5,157,023 A | 10/1992 | Lipton | |
| 5,739,111 A | 4/1998 | Mahe | |
| 5,972,962 A | 10/1999 | Belfield et al. | |
| 6,001,812 A | 12/1999 | Mahe | |
| 2003/0113284 A1 * | 6/2003 | Dalko et al. | ............... 424/70.1 |

FOREIGN PATENT DOCUMENTS

| | | |
|---|---|---|
| EP | 0972 522 A1 | 1/2000 |
| FR | 2784028 | 4/2000 |
| WO | WO 93/01211 | 1/1993 |
| WO | WO/97/10838 | 3/1997 |
| WO | WO/99/58101 | 11/1999 |
| WO | PCT/US00/07846 | 3/2000 |
| WO | WO00/42856 | 7/2000 |
| WO | WO 00/56353 A2 | 9/2000 |
| WO | WO 00/59527 A1 | 10/2000 |

OTHER PUBLICATIONS

Capsoni, F., Meroni, P.L., Zocchi, M.R., Plebani, A.M., Vezio, M., *Effect of Corticosteroids on Neutrophil Function: Inhibition of Antibody–dependent Cell–mediated Cytotoxicity (ADCC)*, J. Immunopharmacol. 5, 217–230 (1983).

Catania, A., Airaghi, L., Garofalo, L., Cutuli, M., Lipton, J.M., *The Neuropeptide α–MSH in HIV Infection and Other Disorders in Humans*, Ann. N.Y. Acad. Sci. 840, 848–856 (1998).

Catania, A., Lipton J.M., α–*Melanocyte Stimulating Hormone in the Modulation of Host Reactions*, 14 Endocr. Rev., 564–576 (1993).

Cutuli, Cristiani, Lipton and Catania, *Antimicrobial effects of α–MSH peptides,* Journal of Leukocyte Biology, vol. 67, Feb. 2000.

Deeter, L.B., et al., *Antipyretic Properties of Centrally Administered α–MSH Fragments in the Rabbit,* Peptides 9, 1285–8 (1989).

Delgado, R., Carlin, A., Alraghi, L., Demitri, M., Meda, L., Galimberti, D., Pierluigi, B., Lipton, J.M., Catania, A., *Melanocortin peptides inhibit production of proinflammatory cytokines and nitric oxide by activated microglia,* 63 J. of Leukocyte Biol. 740 (1998).

Elberle, A. N., *The Melanotropins,* Karger, Basel, Switzerland (1988).

Gow, N.A., *Germ Tube Growth of Candida albicans,* Curr. Topics Med. Mycol. 8, 43–45 (1997).

Hiltz, M.E., Lipton, J.M., *Antiinflammatory activity of a COOH–terminal fragment of the neuropeptide α–MSH,* 3 FASEB J., 2282–2284 (1989).

Hiltz, M.E., *Anti–inflammatory Activity of α–MSH (11–13) Analogs: Influences of Alteration in Stereochemistry,* Peptides 12, 767–71 (1991).

Holdeman, M., et al., *Antipyretic Activity of a Potent α–MSH Analog,* Peptides 6, 273–5 (1985).

Lipton, J.M., Ceriani, G., Macaluso, A., McCoy, D., Carnes, K., Biltz, J., Catania, A., *Anti–inflammatory Effects of the Neuropeptide α–MSH in Acute, Chronic and Systemic Inflammation,* 741 Ann. N.Y. Acad. Sci., 137–148 (1994).

Lipton, J.M., et al., *Anti–inflammatory actions of the Neuroimmunomodulator α–MSH,* Immunol. Today 18, 140–145 (1997).

Macaluso, A., McCoy, D., Ceriani, G., Watanabe, T., Biltz, J., Catania, A., and Lipton, J.M., *Antiinflammatory Influences of α–MSH Molecules: Central Neurogenic and Peripheral Actions,* 14(4), J. of Neuroscience 2377–2382 (1994).

Rajora, N., Boccoli, G., Burns, D., Sharma, S., Catania, A., Lipton, J.M., α–*MSH Modulates Local and Circulating Tumor Necrosis Factor a in Experimental Brain Inflammation,* 17 J. Neurosci, 2181–2186 (1997).

Rajora, N., Ceriani, G., Catania, A., Star, R.A., Murphy, M.T., Lipton, J.M., α–*MSH production, receptors and influence on neopterin, in a human monocyte/macrophage cell line,* 59 H. Leukoc. Biol., 248–253 (1996).

(Continued)

*Primary Examiner*—Jon Weber
*Assistant Examiner*—Sheridan K Snedden
(74) *Attorney, Agent, or Firm*—Perkins Coie LLP

(57) ABSTRACT

The present invention is directed to a treatment for animal pruritis. One aspect of this invention involves a treatment for animal pruritis comprising one or more polypeptides with an amino acid sequence KPV (SEQ ID NO:1), VPK-AC-CC-AC-KPV, HFRWGKPV (SEQ ID NO:3), SYSMEHFR-WGKPV (SEQ ID NO:4) for animal pruritis caused by exposure to any number of agents or causes. The polypeptides are at a level to effectively treat the animal pruritis and are combined with a shampoo. Other combinations include the polypeptides at a level to effectively treat animal pruritis combined with a shampoo and an antibiotic, antifungal and/or and anti-inflammatory. The one or more polypeptides can also be a dimer formed from any of the amino acid sequence above.

8 Claims, 23 Drawing Sheets

OTHER PUBLICATIONS

Richards, D.B., Lipton, J.M. *Effect of α–MSH (11–13) (Lysine–Proline–Valine) on Fever in the Rabbit,* 5 Peptides, 815–817 (1984).

Richards, Mike, DVM at, <http://www.vetinfo.com/dallergy.html> (Jan. 13, 2001).

Scott, D. W., Miller, W. H., Jr.: *Medical Management of Allergic Pruritis in the Cat, with Emphasis on Feline Atopy:* J. S. Afr. Vet. Assoc. 64:103: 1993.

Scott, D. W., Miller, W. H., Jr.: *Nonsteroidal anti–inflammatory Agents in the Management of Canine Allergic Pruritis:* J. S. Afr. Vet. Assoc. 64:52, 1993.

Star, R.A., Rajora, N. Huang, J., Stock, R.C., Catania, A., Lipton, J.M., *Evidence of autocrine modulation of macrophage nitric oxide synthase by α–melanocyte–stimultaing hormone,* 92 Proc. Natl. Acad. Sci., 8016–8020 (1995).

Stevens, D.L., *Could Nonsteroidal Antiinflammatory Drugs (NSAIDs) Enhance in the Progression of Bacterial Infections to Toxic Shock Syndrome?,* Clin. Infect. Dis., 21, 977–80 (1997).

*Allergy: The most common causes of itching in pets:* Cornell University College of Veterinary Medicine Newsletter, Dec. 1999, <http://www.txk9cop.com/allergy.htm>.

*Dr. Roen's Weekly Column,* at <http://www.roen.com/990913.html>.

U.S. Appl. No. 09/533,341, filed Mar. 23, 2000, Catania Anna P. et al.

U.S. Appl. No. 09/535,066, filed Mar. 23, 2000, Lipton, J.M.

U.S. Appl. No. 60/200,287, filed Apr. 28, 2000, Lipton, J.M.

U.S. Appl. No. 09/774,282, filed Jan. 29, 2001, Lipton, J.M.

Airaghi, L., et. al., "Elevated concentrations of plasma α–MSH are associated with reduced disease progression in HIV–infected patients," J. Lab. Clin. Med. 133(3) 309–315 (1999).

Airaghi L, Lettino M, Manfredi MG, Lipton JM, Catania A. Endogenous cytokine antagonists during myocardial ischemia and thrombolytic therapy. Am. Heart J. 130: 204–211, 1995.

Airaghi L. Garofalo L. Cutuli MG. Delgado R. Carlin A. Demitri MT. Badalamenti S. Graziani G. Lipton JM. Catania A. Plasma concentrations of α–melanocyte–stimulating hormone are elevated in patients on chronic haemodialysis. Nephrology Dialysis Transplantation 15:1212–1216, 2000.

Baker, M., et. al., "The Relationship between Interleukin–6 and Herpes Simplex Virus Type–I: Implications for Behavior and Immunopathology," *Brain Behav. Immun.* 13(3):201–11 (1999).

Barker, et al., "Principles of Ambulatory Medicine," *Williams and Wilkins (1982).*

Barcellini, W., et al., "Inhibitory Influences of α–MSH peptides on HIV–1 expression in Monocytic cells," 12th World AIDS Conference Geneya, Abstract No. 60685, Jun. 28–Jul. 3, 1998.

Barcellini W, La Maestra L, Clerici G, Garofalo L, Brini AT, Lipton JM, Catania A. α–MSH peptides inhibit HIV–1 expression in chronically infected promonocytic U1 cells and in acutely infected monocytes. Journal of Leukocyte Biology 68:693–699, 2000.

Bhattacharya A., et. al., "Effect of Cyclic AMP on RNA and Protein Synthesis in *Candida albicans,*" *Biochem. Biophysics. Res. Commun.,* 77: 1438–44 (1977).

Bickers, D., Sun–Induced Disorders, *Emergency Medicine Clinics of North America,* 3(4): 659–663, 660 (1985).

Cartledge, J.D., et. al., "Clinically Significant Azole Cross–Resistance in *Candida* Isolates from HIV–Positive Patients with Oral Candidosis," *AIDS* 11:1839–44 (1997).

Catania, A., et. al., "Melanocortin Peptides Inhibit Production of Proinflammatory Cytokines in Blood of HIV–Infected Patients," *Peptides,* 19(6): 1099–1104 (1998).

Catania, A.; et. al., "The Neuropeptide α–MSH has Specific Receptors on Neutrophils and Reduces Chemotaxis in Vitro," *Peptides*17, 675–679 (1996).

Catania A, Airaghi L, Lipton JM. α–MSH in normal human physiology and disease states. Trends Endocrinol. Metab. 11:304–308, 2000.

Catania A, Delgado R, Airaghi L, Cutuli M, Garofalo L, Carlin A, Demitri MT, Lipton JM. α–MSH in systemic inflammation: central and peripheral actions. Annals of the New York Academy of Sciences, 885:183–187, 1999.

Catania A, Grazia M, Manfredi MG, Airaghi L, Ceriani G, Gandino A, Lipton JM. Cytokine antagonists in infectious and inflammatory disorders. Annals of the New York Academy of Sciences 741: 149–161, 1994.

Catania A, Lipton JM. α–melanocyte–stimulating hormone peptides in host responses: from basic evidence to human research. Annals of the New York Academy of Sciences 680: 412–423, 1993.

Catania A, Cutuli M, Garofalo L, Airaghi L, Valenza F, Lipton JM, Gattinoni L. Plasma concentrations and anti–L–cytokine effects of α–melanocyte stimulating hormone in septic patients. Crit. Care Med. 28: 1403–1407, 2000.

Catania A, Airaghi L, Motta P, Manfredi MG, Annoni G, Pettenati C, Brambilla F and Lipton JM. Cytokine antagonists in aged subjects and their relation with cellular immunity. Journal of Gerontology: Biological Sciences 52A: B93–97, 1997.

Catania A, Manfredi MG, Airaghi L, Vivirito MC, Capetti A, Milazzo F, Lipton JM and Zanussi C. Plasma concentration of cytokine antagonists in patients with HIV infection. Neuroimmunomodulation 1: 42–49, 1994.

Catania A, Airaghi L, Manfredi MG, Vivirito MC, Milazzo F, Lipton JM, Zanussi C: Proopiomelanocortin–derived peptides and cytokines: relations in patients with acquired immunodeficiency syndrome. Clinical Immunology and Immunopathology 66: 73–79, 1993.

Cavallo, J. and Deleo, V., Sunburn, *Dermatologic Clinics,* 4(2): 181–187, 181 (1986).

Ceriani, G., et al., "Central Neurogenic Antiinflammatory Action of α–MSH: Modulation of Peripheral Inflammation Induced by Cytokines and other Mediators of Inflammation," *Neuroendocrinology,* 59:138–143 (1994).

Ceriani G, Diaz J, Murphree S, Catania A, Lipton JM. The neuropeptide alpha–melanocyte–stimulating hormone inhibits expreimental arthritis in rats. Neuroimmunomodulation 1:28–32, 1994.

Chiao H, Foster S, Thomas R, Lipton J, and Star RA. α–MSH reduces endotoxin–induced liver inflammation. J. Clin. Invest. 97: 2038–2044, 1996.

Csata, M. et al., "Enhancement of *Candida albicans* killing activity of separated human epidermal cells by alpha–melanocyte stimulating hormone," British Journal of Dermatology, 121(1) 145–147 (1989).

Domk–Optiz, I., et. al., "Stimulation of Macrophages by Endotoxin Results in the Reactivation of a Persistent Herpes Simplex Virus Infection," *Scand. J. Immunol.* 32(2):69–75 (1990).

Eberle, A. and Schwyzer, R., Hormone–Receptor Interactions, *Clinical Endocrinology* 5, Suppl., 41s–48s (1976).

Fauci, A.S., "Host Factors in the Pathogenesis of HIV–induced Disease," *Nature* 384: 529 (1996).

Fitzpatrick, et al., Acute Effects of Ultraviolet Radiation on the Skin: The Sunburn Reaction, *Dermatology in General Medicine,* 4th Edition, 1651–1655, 1651 (1993).

Fitzpatrick, et al., "Color Atlas and Synopsis of Clinical Dermatology," (1983).

Foster, J. Sunburn, *eMedicine—Online Medical Reference Textbook,* (last modified May 1, 2000), <http://emedicine.com/emerg/topic798.htm.

Fox, J. A., et.al., "Immunoreactive α–Melanocyte Stimulating Hormone, Its Distribution in the Gastrointestinal Tract of Intact and Hypophysectomized Rats," *Life. Sci.* 28, 2127–2132 (1981).

Galimberti D, Baron PL, Meda L, Prat E, Scarpini E, Delgado R, Catania A, Lipton JM, Scarlato G. α–MSH peptides inhibit production of nitric oxide and tumor necrosis factor–α by microglial cells activated with β–amyloid and interferon γ. Biochemical Biophysical Research Communications 263: 251–256, 1999.

Getting, et al., POMC Gene–Derived Peptides Activate Melanocortin Type 3 Receptor on Murine Macrophages, Suppress Cytokin Release, and Inhibit Neutrophil Migration in Acute Experimental Inflammation, J. Immunol., vol. 162, No. 12, pp. 7446–7453 (1999).

Harris et al., Alpha–melanocyte stimulating hormone (a–MSH) and melanin–concentrating hormone (MCH) stimulate phagocytosis by head kidney leucocytes of rainbow trout (*Oncorhynchus mykiss*) in vitro, Fish & Shell Immunol., vol. 8, 8:631–638 (1998).

Hart, D.A., et. al., "*Staphylococcus Aureus* Strains Differ in Their in Vitro Responsiveness to Human Urokinase: Evidence that Methicillin–Resistant Strains are Predominantly Nonresponsive to the Growth–Enhancing Effects of Urokinase," *Can. J. Microbiol.* 42: 1024–31 (1966).

"Harry's Comseticology", *Chemical Publishing,* 7th ed. (1982).

Hiltz, M.E., et. al., "Alpha–MSH Peptodes Inhibit Acute Inflammation and Contact Sensitivity," *Peptides,* 11:979–982 (1990).

Hiltz, M.E., et. al., "α–MSH Peptides Inhibit Acute Inflammation Induced in Mice by rIL–1β, rIL–6, rTNF–α and endogenous pyrogen but not that cause by TLB4, PAF and rIL–8," *Cytokine* 4(4):320–328 (1992).

Huang, et al., Role of central melanocortins in endotoxin–enduced anorexia, Am. J. Physio (Regulatory, Integrative & Comparative Physiology, vol. 276, No. 3, pp. R864–R871 (1999).

Huh S–K, Lipton JM and Batjer HH. The protective effects of α–melanocyte stimulating hormone on canine brainstem ischemia. Neurosurgery 40:132–139, 1997.

Ichiyama T, Sakai T, Catania A, Barsh GS, Furukawa S, Lipton JM. Systemically administered α–melanocyte–stimulating hormone peptides inhibit NF–κB activation in experimental brain inflammation. Brain Research 836: 31–37, 1999.

Ichiyama T, Zhao H, Catania A, Furukawa S, Lipton JM. α–melanocyte–stimulating hormone inhibits NF–κB activation and IαBκ degradation in human glioma cells and in experimental brain inflammation. Experimental Neurology 157:359–365, 1999.

Ichiyama T, Campbell IL, Furukawa S, Catania A, Lipton JM. Autocrine α–melanocyte–stimulating hormone inhibits NF–κB activation in human glioma cells. Journal of Neuroscience Research 58:684–689, 1999.

Ichiyama T, Okada K, Campbell IL, Furukawa S, Lipton JM. NF–κB activation is inhibited in human pulmonary epithelial cells transfected with α–melanocyte–stimulating hormone vector. Peptides 21: 1473–1477, 2000.

Ichiyama T, Sakai T, Catania A, Barsh GS, Furukawa S, Lipton JM. Inhibition of peripheral NF–κB activation by central action of α–melanocyte–stimulating hormone. Journal of Neuroimmunology 99: 211–217, 1999.

Lichtensteiger, W., and Monnet, F., "Differential Response of Dopamine Neurons to α–Melanotropin and Analogues in Relation to Their Endocrine and Behavioral Potency," *Life Sci.* 25:2079–2087 (1979).

Lipton, J.M., "Neuropeptide α–Melanocyte–Stimulating Hormone in Control of Fever, the Acute Phase Response, and Inflammation," *Neuroimmune Networks: Physiology and Diseases,* (Alan R. Liss, Inc. 1989) pp. 243–250.

Lipton, J.M., Modulation of Host De Neuropeptide α–MSH, *The Yale Journal of Biology and Medicine* 63: 173–182 (1990).

Lipton JM, Catania A, Ichiyama T. Marshalling the anit–inflammatory influence of the neuroimmunomodulator α–MSH. News Physiol. Sci, 15: 192–195, 2000.

Lipton JM, Catania A. The neuropeptide α–MSH: a modulator of host reactions. Seminars in Clinical Immunology 10: 25–29, 1995.

Lipton, et al., Mechanisms of antiinflammatory action of the neuro immunomodulatory peptide alpha–MSH, Annals of the N.Y. Acad. Sci., vol. 840, pp. 373–380 (1998).

Luger, T.A., et. al., "Production of Immunosuppressing Melanotropins by Human Keratinocytes," *Ann. N.Y. Acad. Sci.* 680: 567–570 (1993).

Lyson, K., et. al., "Binding of Anti–Inflammatory α–Melanocyte–Stimulating Hormone Peptides and Proinflammatory Cytokines to Receptors on Melanoma Cells," *Neuroimmunomodulation,* 1:121–126 (1994).

Mayhall, Ten Home Remedies for Sunburn, *Seasonal Health,* (Jul. 14, 2000), <http://drkoop.com/wellness/seasonal/summer/sunburn.html>.

Mugridge, K.G., et. al., "α–Melanocyte–Stimulating Hormone reduces interleukin–1β effects on rat stomach preparations possibly through interference with type I receptor," *European Journal of Pharmacology,* 197: 151–155 (1991).

Noisakran S., e. al., "Lymphocytes Delay Kinetics of HSV–1 Reactivation from in vitro Explants of Latent Infected Trigeminal Ganglia," *J. Neuroimmunol.* 95(1–2):126–35 (1999).

Patel, A., et. al., "Herpes Simplex Type 1 Induction of Persistent NF–κB Nuclear Translocation Increases the Efficiency of Virus Replication," *Virology* 247(2):212–22 (1998).

Potts, Sunlight, Sunburn, and Sunscreens, *Postgrad. med.,* 87:52–61 (1990).

Rajora N, Boccoli G, Catania A and Lipton JM. α–MSH modulates experimental inflammatory bowel disease. Peptides 18:381–385, 1997.

Remington's Pharmaceutical Sciences, *Mack Publishing Co.,* 18th ed. (1990).

*Robbins Pathologic Basis of Disease* 5th *ed.,* Saunders Co., Philadelphia (1994) p. 335–337, 354–355, 1008, 1037–1038.

Ryan, et al., "Inflammation," *a Scope Publication, The Upjohn Company,* (1977).

Szalay, K.S., et. al., "Structure–activity studies with ACTH/ α–MSH fragments on corticosteroid secrection of isolated zona glomerulosa and fasciculata cells," *Regulatory Peptides,* 11: 187–192 (1985).

Taherzadeh S, Sharma S, Chhajlani V, Gantz I, Rajora N, Demitri MT, Kelly L, Zhao H, Catania A, Lipton JM. α–MSH and its receptors in regulation of tumor necrosis factor–α production by human monocyte/macrophages. Am. J. Physiol. 276: R1289–R1294, 1999.

Thody, A.J., et.al., "MSH Peptides are Present in Mammalian Skin," *Peptides* 4, 813–815 (1983).

Uehara, Y., et. al., "Carboxyl–terminal tripeptide of α–Melanocyte–Stimulating Hormone anagonizes interleukin–1–induced anorexia," *European Journal of Pharmacology,* 220: 119–122 (1992).

van Nispen, J.W. and Greven, H.M., "Structure–Activity Relationships of Peptides Derived From ACTH, β–LPH and MSH With Regard To Avoidance Behavior in Rats," *Pharmac. Ther.* 16: 67–102 (1982).

Walev, I., et.al., "Enhancement by TNF–alpha of Reactivation and Replication of Latent Herpes Simplex Virus from Trigeminal Ganglia of Mice," *Arch Virol.* 140(6):987–92 (1995).

Watanabe T, Hiltz ME, Catania A, Lipton JM. Inhibition of IL–1β–induced peripheral inflammation by peripheral and central administration of analogs of the neuropeptide α–MSH. Brain Research Bulletin 32: 311–314, 1993.

Weiss, et al., Corticotropin–peptide regulation on intracellular cyclic–AMP production in cortical neurons in primary culture, J. Neurochem. vol. 45, No. 3, pp. 869–874 (1985).

Wenzel, R.P. and Pfaller, M.A., "*Candida* Species: Emerging Hospital Bloodstream Pathogens," *Infect. Control. Hosp. Epidemiol.* 12: 523–4 (1991).

Wong, K.Y., et. al., "A Potential Mechanism of Local Anti–inflammatory Action of Alpha–Melanocyte–Stimulating Hormone within the Brain: Modulation of Tumor Necrosis Factor–Alpha Production by Human Astrocytic Cells," *Neuroimmunomodulation,* 4:37–41 (1997).

"Vaginitis," National Institute of Child Health and Human Development—Publications On–line (last modified Jan. 12, 2000).<www.nichd.nih.gov/publications/pubs/vagtoc.html>.

"Tampons and Asbestos, Dioxins, & Toxic Shock Syndrome," FDA Center for Devices and Radiological Health (Jul. 23, 1999), <http://www.fda.gov/cdrh/ocd/tamponsabs.html>.

Khurshid, M.A., et. al., :*Staphylococcus aureus* with Reduced Susceptibility to Vancomycin—Illinois, 1999, *Morbidity and Mortality Weekly Report,* 48(51): 1165–1167 (2000), <http://www.cdc.gov/epo/mmwr/preview/mmwrhtml/mm4851al.htm>.

"Women's Health, Urinary Tract Infections: A Patients Guide to Treatment," *AMA Health Insight, On–Line Health Information for Everyone* (last updated Oct. 30, 1998) <http://www.ama–assn.org/insight/h_focus/wom_hlth/uti/uti.htm>.

U.S. Appl. No. 09/957,765, filed Sep. 21, 2001, Catania, Anna et al.

Luger et al., "The Role of alpha–MSH as a Modulator of Cutaneous Inflammation," Annals New York Acad. Sci. 2000, vol. 917, pp. 232–238.

PCT International Search Report for International Application No. PCT/US02/40313, dated May 30, 2003, 5 pages.

* cited by examiner

USE OF A POLYPEPTIDE FOR TREATMENT OF PRURITIS IN ANIMALS

FIELD OF INVENTION

The present invention relates to a method of treating pruritis in animals with formulations including a polypeptide having a KPV or a functionally equivalent amino acid sequence.

BACKGROUND OF INVENTION

Animal pruritis (itching) is a common affliction effecting domesticated animals and livestock alike. α MSH and/or its derivatives have shown effectiveness in inflammatory conditions and the sequelae of those inflammatory conditions. See, Lipton, J. M., et al., *Anti-inflammatory Influence of the Neuroimmunomodulator α-MSH, Immunol. Today* 18, 140–145 (1997). Pruritis is a frequent element of inflammation. Any number of diseases or conditions can cause it. Everything from fleas to allergies can be the base cause but the result is same, i.e. excoriation (badly scratched skin), vesicular and papular rashes (rashes made up of varying sizes of blisters), erythema (reddening of the skin) hair loss, scaling, open lesions secondary to excoriation and opportunistic infection of open lesions.

Pruritis is the most common veterinary sign in animal dermatology. In humans, pruritis manifests as a symptom that most times a person can relate to a caregiver. In an animal, the pruritis presents as a sign in either a epicritic (localized) distribution or in a protopathic (poorly localized) distribution which is communicated to an owner via scratching, agitation, hair loss, or, sometimes, auto-inflicted wounds.

Pruritis is the result of chemical reactions occurring in the skin of the animal that result in nociceptor activation of afferent fibers in the nerves. Some of the chemicals mediators involved are prostaglandins, arachodonic acid, proteolytic enzymes, cytokines, histamine, seratonin, platelet activating factor, kallikrein, bradykinin, substance P and leucotrienes. A universal mediator to explain pruritis has not been found. See, Goldsmith, L. A. (Ed.) *Physiology, Biochemistry and Molecular Biology of the Skin*, $2^{nd}$ ed. Oxford University Press. It has been asserted, on the basis of studies performed on humans, that proteolytic enzymes are the most important mediators of pruritis in dogs and cats. Clinical studies have suggested that histamine and leukotrienes are important in cats and dogs. See, Scott, D. W., Miller, W. H., Jr.: *Nonsteroidal anti-inflammatory Agents in the Management of Canine Allergic Pruritis:* J. S. Afr. Vet. Assoc. 64:52, 1993; Scott, D. W., Miller, W. H., Jr.: *Medical Management of Allergic Pruritis in the Cat, with Emphasis on Feline Atopy:* J. S. Afr. Vet. Assoc. 64:103: 1993. As these are the same chemicals affecting the inflammatory reaction, controlling inflammation is one way to ameliorate pruritis that results from the actions on the nerves of the various chemicals.

Those pruritic conditions that are the result of secondary sources, like fleas for example, are curable. Unfortunately, primary causes of pruritis, such as auto-immune diseases, are chronic and can not be cured. See, Columbia Animal Hospital School of Medicine, at <http://www.cah.com/medicine.html>. In this case the disease requires frequent or lifelong treatment. A well-tolerated treatment with minimal or no side effects would be a great advantage.

The causes, whether secondary or primary, of animal pruritis, are numerous. By far, allergies are the most common cause. Other common causes include, but are not limited to, hormonal hypersensitivities, food hypersensitivity, bacterial, fungal or parasitic hypersensitivity, auto-immune disorders and other glandular disorders.

Allergies are manifested as the result of numerous allergens. The most common is allergy to flea saliva. Certain animals become sensitized to components of flea saliva. Thereafter, each fleabite stimulates an allergic reaction that results in intense pruritis, erythema and papules. These changes can be localized or generalized, and are usually apparent around the base of the tail and spine, inner thighs and on the abdomen. This problem is affected by the seasons; as much because of the number of possible fleabites in different seasons as by the animal's natural response to different climate conditions. Further, the reaction is worse in older animals.

Because allergy to fleas is a hypersensitivity reaction and not simply a response to the number of bites, the severity of the pruritis and the skin changes are not necessarily proportional to the number of fleas. In other words, one fleabite on a highly sensitized animal may produce a severe reaction. See, Scott, Miller & Griffen, *Muller & Kirk's Textbook of Animal Dermatology* $5^{th}$ Ed. W. B Saunders Company (1995). The inability to demonstrate fleas or flea dirt on the animal in no way precludes the diagnosis. A compound directed at both ridding the animal of fleas and alleviating that animal's reaction to its hypersensitivity would be beneficial.

Mange, a parasitic condition, is a veterinary problem similar to fleabite hypersensitivity. This common infection is result of either *Sarcoptes Scabei* or *Demodex Canis*. Untreated mange can result in loss of hair, erythema, agitation, flaking and crusting of the skin, and auto-mutilation. Treatment is usually effective but can be time consuming—several months in duration—and tedious, with multiple shampoos, dips, insecticides and clipping. An anti-pruritic addition to this therapy would make the long-term course more effective with limitation of auto-mutilation through increased comfort to the animal.

An additional and common cause of pruritis in animals is atopy. This is a generalized type of inhalant allergy. It is the second most common allergic skin disease in dogs. It also can be seen in cats but is noticed on a much less frequent basis. See, *Cornell University College of Veterinary Medicine Newsletter*, December 1999, <http://www.txk9cop.com/allergy.htm>. Further, this disease, which is believed to be the result of an autosomal recessive trait, shows varying penetration in different breeds of the same species.

The disease commonly starts by the third year of age. In the primary stages of the disorder, the pruritis is seasonal and is associated with only one or two seasons of the year. However, the pruritis becomes recalcitrant as the animal grows older and may last all year long. Glucocorticoid therapy has been the treatment of choice to control the pruritis and inflammation. Discussed below, steroids have many untoward side effects. Some of these side effects may be dangerous for the animal.

In the case of atopy, an anti-pruritic treatment may be needed while a search for the allergens and subsequent desensitization procedures are performed. Allergens that cause a more intense epicritic or protopathic reaction in the animal may be controlled in degree by variable dose related therapy. In this way, the graded treatment of the pruritis would not interfere with the differential diagnosis of allergens while making the duration of the diagnostic process more tolerable to the animal.

Many animals may suffer from food allergies. Additionally, the specific food the animal is allergic to may be one that animal has eaten for some time and has slowly developed a sensitivity. Large protein molecules often are the source of the food allergy. See, *Dr. Roen's Weekly Column*, at <http://www.roen.com/990913.html>.

These allergies manifest as dermatological problems and not as gastroenteric problems. For example, the great majority of dogs with food allergy have pruritus and lack any other dermatological changes or gastrointestinal disease whatsoever. Once the pruritis is traced to a food allergy, the veterinarian commences the search for the specific allergen. Again, once the allergen is found, the use of an anti-pruritic is helpful during the process of desensitization. This keeps the animal comfortable and avoids damage to the skin of the animal through excoriation.

Hormonal hypersensitivity is a rare condition in some animals causing severe pruritis. In this case, the animal is allergic to its own hormones. This is usually a "self-limiting" type of disorder, i.e. it runs a particular, though often not predictable, course. Commonly the disease appears during estrus (heat in dogs, for example). Because the pruritis disappears spontaneously when the estrus is over, treatment is only needed for that period of active pruritis. A treatment with little or no side effects would be a desired course.

Bacterial and fungal skin infections are another common cause of pruritis in animals. *Staphylococcus* sp., are the most common microorganisms found in the bacterial skin diseases. In fungal disease (commonly referred to as "ringworm") *Microsporum* sp., and *Trycophyton* sp., are the most common fungal organisms. *Candida Albicans* is yet another example of an fungus that infects animals and causes pruritis. Although these are all common to the flora of animal skin, they are also opportunistic pathogens capable of infecting the animal skin given the right conditions.

Antibiotic treatments, whether alone or in combination with fungicides or glucocorticoids, suffer many of the same deficiencies as glucocorticoid treatments. Glucocorticoid treatment tends to promote growth of microbes. Antibiotic sensitivities may further contribute to the pruritis the antibiotics are administered to treat. Antibiotic treatments are expensive and require animal supervision and strict compliance. In the commercial livestock context, antibiotics affect food and water consumption and voiding and may cause a loss of muscle mass.

As noted above, bacterial infection is one of the common sequelae of pruritis in that the animal may open a wound secondary to excoriation. Further, the bacterial infection may be the result of parasitism or general immune deficiency. A combination for treatment including antipruritic and/or antibacterial and antifungal properties would be beneficial to the animal suffering from bacterial or fungal based pruritis.

Treatments for the various causes of pruritis are as varied as the causes of the pruritis. The range of treatments varies in relation to the severity and etiology of the disorder causing the pruritis. For example, cold water can produce temporary relief in simple epicritic-type pruritis. Longer relief can be obtained by using additives with the water. Common additives include different varieties of oatmeal-based shampoos or cream rinses, and Domeboro® solution or Aveeno® used as rinses. Certain other shampoo treatments, depending on the etiology of the pruritis, contain an antibacterial agent, salicylic acid, tar and fatty acids. These methods, as mentioned, are only temporary and not well suited for compliance. Still, therapeutic shampoos remain an important part of a number of treatment protocols. See, Mike Richards, DVM at, <http://www.vetinfo.com/dallergy.html>(Jan. 13, 2001).

As the pruritis becomes more severe, or is the result of a more complicated origin, the treatments become more complicated. When treatments become more medicinal or invasive the potential for complications and side effects naturally increase. One medicinal treatment is to use either prescription or over-the-counter antihistamines. Often the antihistamines are combined with fatty acid inhibitors. Used alone, about 15 to 25% of dogs will respond to antihistamines and in combination with fatty acid inhibitors show only an efficacy of up to 40%. Most animals, while showing some level of reduction in scratching behavior, show lethargy or drowsiness and drying of mucous membranes. Some animals are known to show paradoxical agitation with antihistamines. See, Id.

Fatty acid derivatives that compete with arachadonic acid (a known trigger for pruritis) and replace it with an inactive competitor are useful, in high doses, against certain types of pruritis. Unfortunately, these medicines must be used for months and are only available through a veterinarian. Additionally, they are very expensive.

In spite of the tediousness, time consumption, and expense of the above medications and treatments, they are preferable to injection therapy or the next most common line of treatment which is glucocorticoid therapy.

Oral or parenteral glucocorticoids are often used in complicated or uncontrolled pruritis. Although the medications are often effective, they have many unfortunate side effects in long term use. They can: increase thirst resulting in increased voiding; increase appetite, resulting in difficulty in weight control; decrease bone density; increased occurrences chance of pancreatitis; cause immunosuppression via lymphocyte depression with increased risk of secondary infection; induce Cushing's disease; hair loss; variations in hormonal control of water balance; and, muscle weakness. These potential complications require frequent visits to or by the veterinarian to monitor the animal on steroid therapy. Further, topical steroid use has multiple drawbacks. For example, topical steroid use for as little as two weeks can cause: 1) telangiectasia (dilation of capillaries and sometimes of terminal arteries producing an angioma of macular appearance, or hyperemic spot); 2) skin atrophy or thinning of the skin; and 3), mask an infection or suppress the host response to invasion by opportunistic pathogens.

This latter point, whether from intralesional injection, oral, parenteral or topical use, is of great importance in any dermatological disorder that may result in an open lesion. Open lesions are a notoriously favorable environment for opportunistic infection. The warmth, blood supply, pH, and necrotic tissue are all conducive to bacterial or fungal colonization. Using a steroid in this environment may slow the response to an infection and thereby mask commonly observed and treated signs of an infection; namely, purulence or pus., Thus, a simple infection in the presence of a topical steroid can be masked to the point of serious infection and sepsis.

Reduced killing of pathogens is a detrimental consequence of therapy with anti-inflammatory drugs. In addition to its potent anti-inflammatory effects, α-MSH and/or its derivatives have anti-microbial efficacy as well. α-MSH and/or its derivatives inhibits common skin pathogens, i.e. *Staphylococcus Aureus* and *Candida Albicans*, show bactericidal and fungicidal properties, respectively. See, Cutull, Cristiani, Lipton and Catania, *Antimicrobial Effects of α MSH Peptides,* Journal of Leukocyte Biology, Volume 67, February 2000.

It follows that the use of a preparation that could offer all the benefits of steroid preparations, shampoos and other soothing agents, but without the attendant side effects and with a more facile tolerance and compliance, will be a great addition to the available avenues of treatment of these disorders.

Based on the foregoing, a preferred composition for the treatment of pruritis would be anti-inflammatory without causing immunosuppression. A preferred composition would also have antibiotic and antifungal properties with little to no immuno-cross-reactivity i.e., it would be hypoallergenic. A preferred composition would also be therapeutically effective at low concentrations and have little effect on appetite, muscle mass, and water balance so that it would be commercially practicable to the livestock industry.

SUMMARY OF THE INVENTION

The invention includes a composition and method of treatment of animal pruritis. A preferred embodiment of the invention is composition for the treatment of animal pruritis comprising a therapeutically effective amount of one or more peptides having a COOH-terminal sequence consisting of KPV (SEQ ID NO:1), MEHFRWG (SEQ ID NO:2), HFRWGKPV (SEQ ID NO:3), and SYSMEHFRWGKPV (SEQ ID NO:4) in combination with a shampoo.

The one or more polypeptides may be a dimer formed from any of the amino acid sequences above. The dimer, KPV-Ac-CC-Ac-KPV (Ac=Acetyl group), is N-acetylated and C-amidated. Dimers can be formed by adding cysteines at the N-termini of any of the above polypeptides and allowing the cysteines of two polypeptides to form a disulfide bond. Both homo-dimers and hetero-dimers can be formed using this method.

Another preferred embodiment of the invention is a composition for the treatment of animal pruritis comprising a therapeutically effective amount of one or more of these peptides in combination with a therapeutically effective amount of an anti-inflammatory and a shampoo.

In another embodiment of the invention each of these compositions may further comprise a therapeutically effective amount of an antibiotic.

In another embodiment of the invention each of these combination compositions may further comprise a therapeutically effective amount of an antifungal.

The peptides in each of these preferred combination compositions has the primary sequence of KPV (SEQ ID NO:1) or VPK-Ac-CC-Ac-KPV. In a preferred composition, pharmacologically effective concentrations of the peptides may be as low as $10^{-12}$M but maybe as high $10^{-4}$M.

ANOTHER EMBODIMENT OF THE INVENTION IS A METHOD TO TREAT ANIMAL PRURITIS COMPRISING TOPICAL OR SYSTEMIC ADMINISTRATION OF ONE OR MORE OF THE PREFERRED PEPTIDES.

The most effective of the melanocortin peptides were those including the C-terminal amino acid sequence of α-MSH, namely, α-MSH (1–13), α-MSH (6–13) and α-MSH (11–13).

Figure 3:
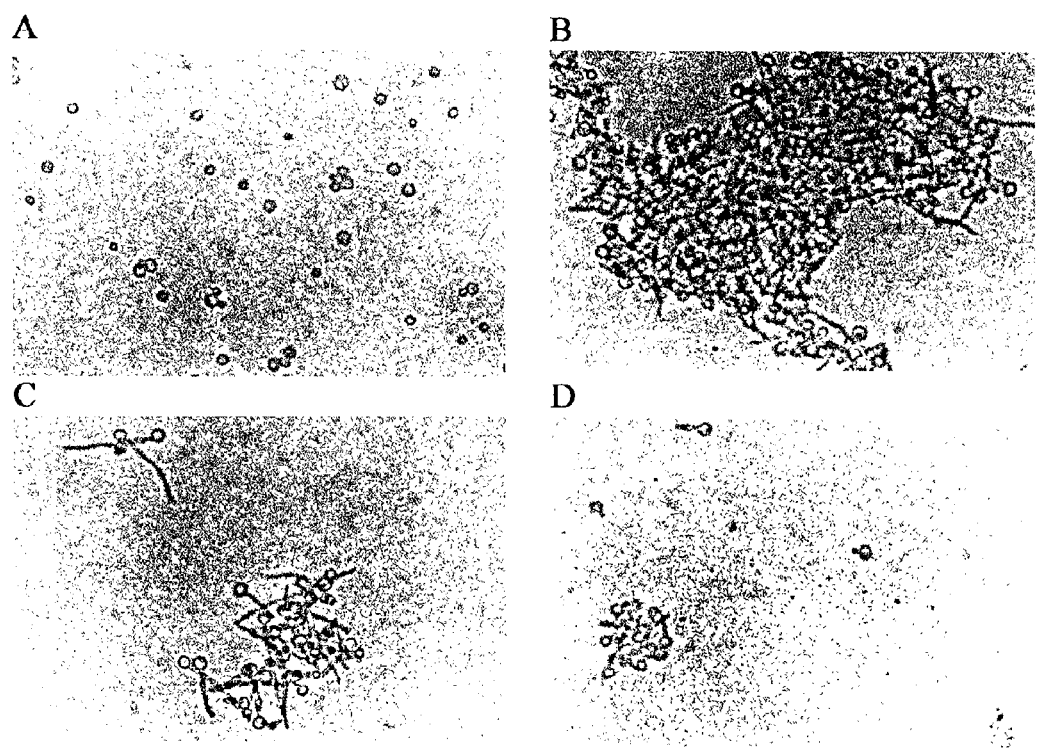

FIG. 3A shows untreated germination of *C. albicans*, i.e. blastopores.

FIG. 3B shows a horse serum-induced germination of *C. albicans*.

FIG. 3C shows the effect of α-MSH (1–13) treatment on germination of *C. albicans*.

FIG. 3D shows the effect of α-MSH (11–13) treatment on germination of *C. albicans*.

Figure 4:
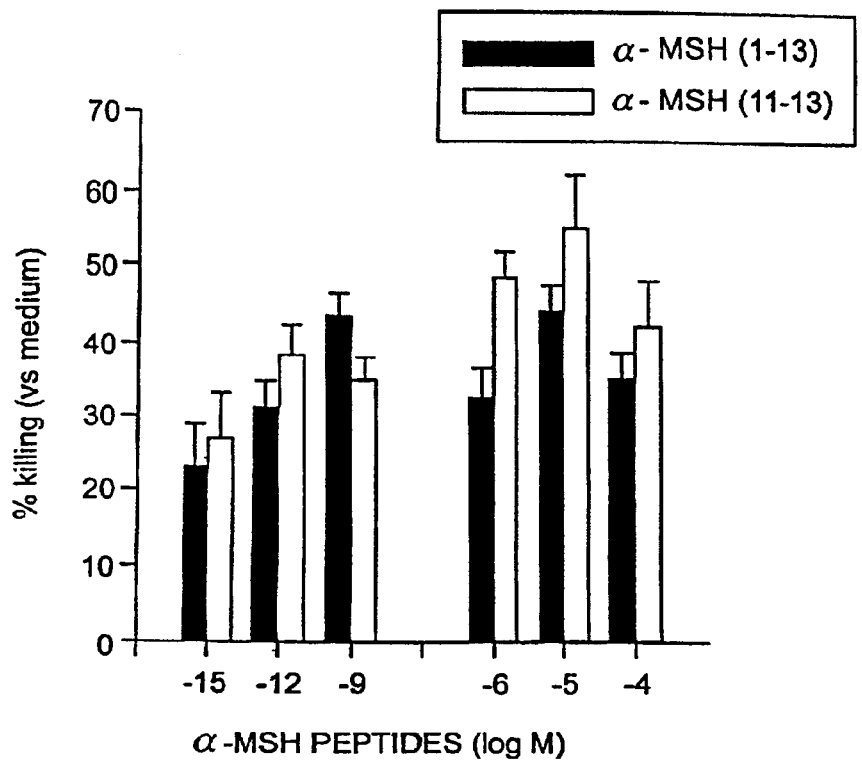

FIG. 4 illustrates the effect of α-MSH (1–13) and α-MSH (11–13) on *C. albicans* killing by human neutrophils. Values are expressed as percent increase in killing vs. medium. Scores are means±SEM.

Figure 5:
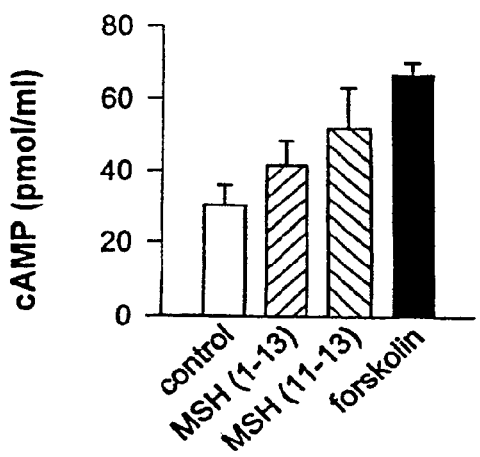

FIG. 5 illustrates the effect of α-MSH (1–13), α-MSH (11–13), and forskolin on cAMP content of *C. albicans*.

Figure 6:
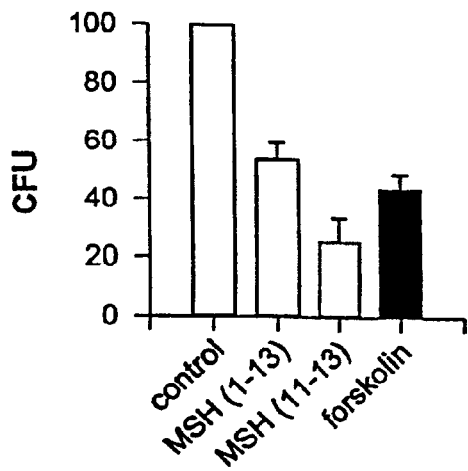

FIG. 6 illustrates the inhibitory effect of α-MSH (1–13), α-MSH (11–13), and forskolin on *C. albicans* colony forming units.

Figure 7:
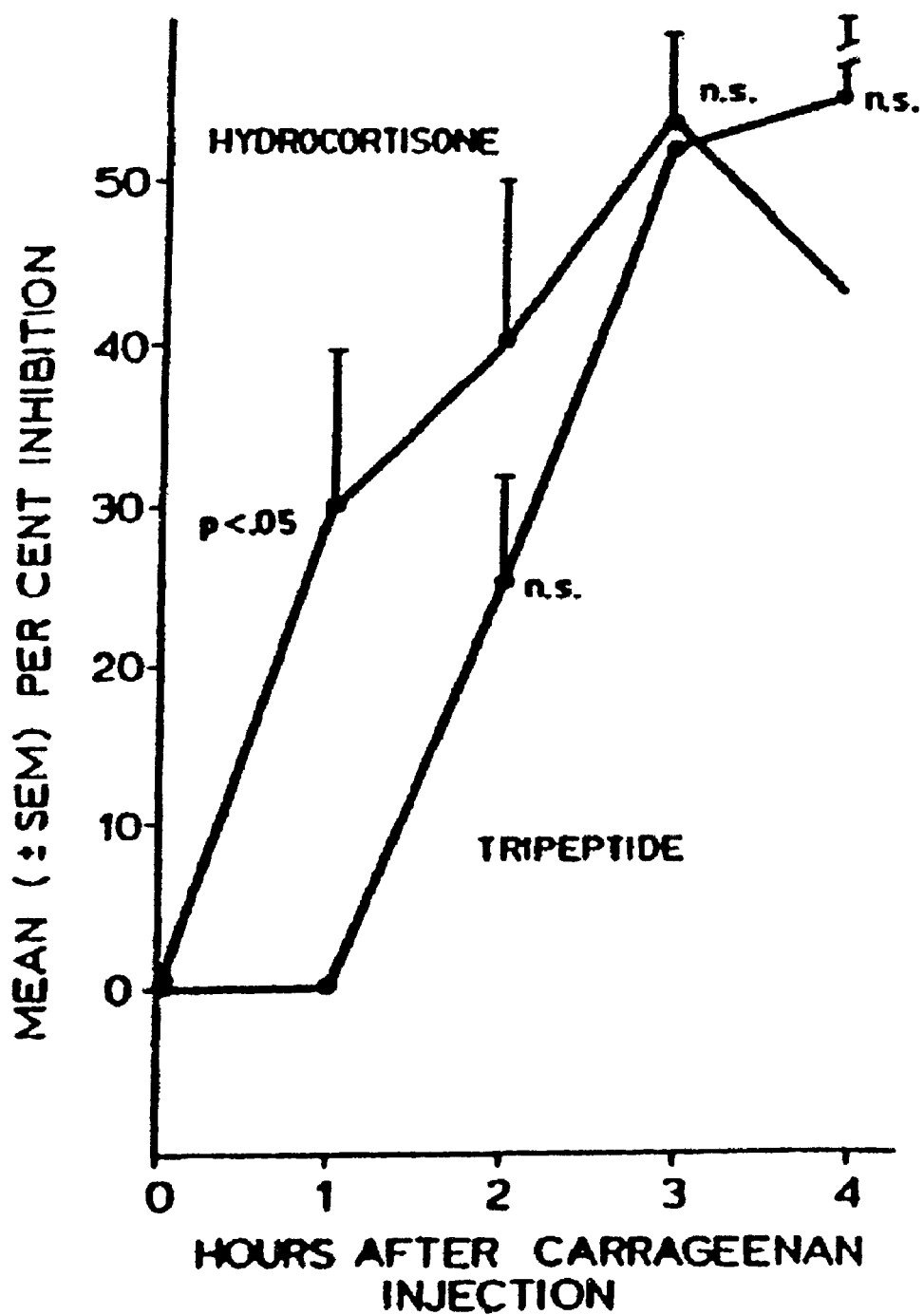

FIG. 7 illustrates the anti-inflammatory effects α-MSH (11–13) relative to hydrocortisone on edema caused by injection of carageenan. Scores are mean±SEM differences from baseline measures for control and peptide treatments.

Figure 8:
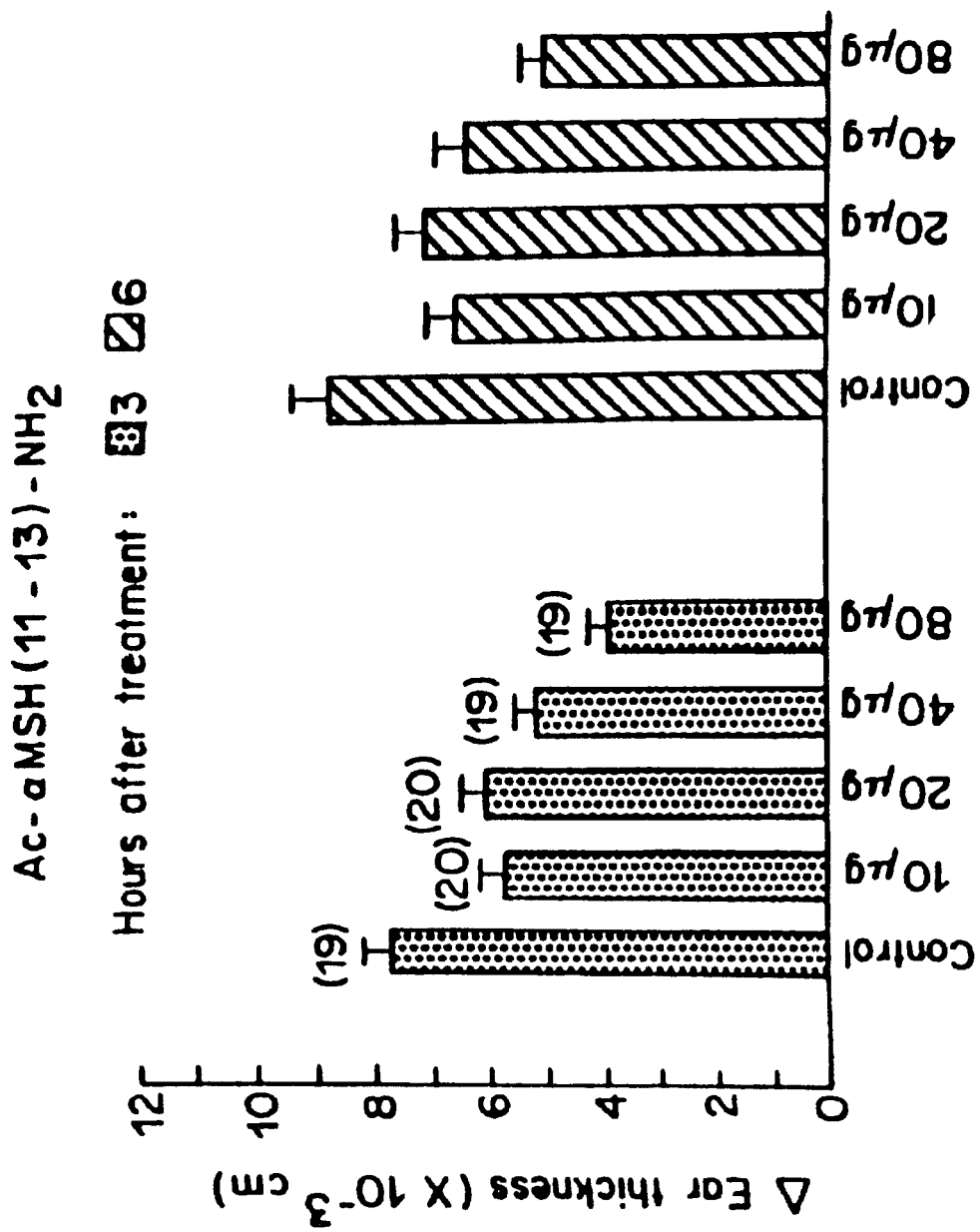

FIG. 8 illustrates inhibition by α-MSH (11–13) of inflammation induced in the ear by picryl chloride application. Scores are mean±SEM differences from baseline measures for control and peptide treatments. Number of animals shown in parentheses.

Figure 9:
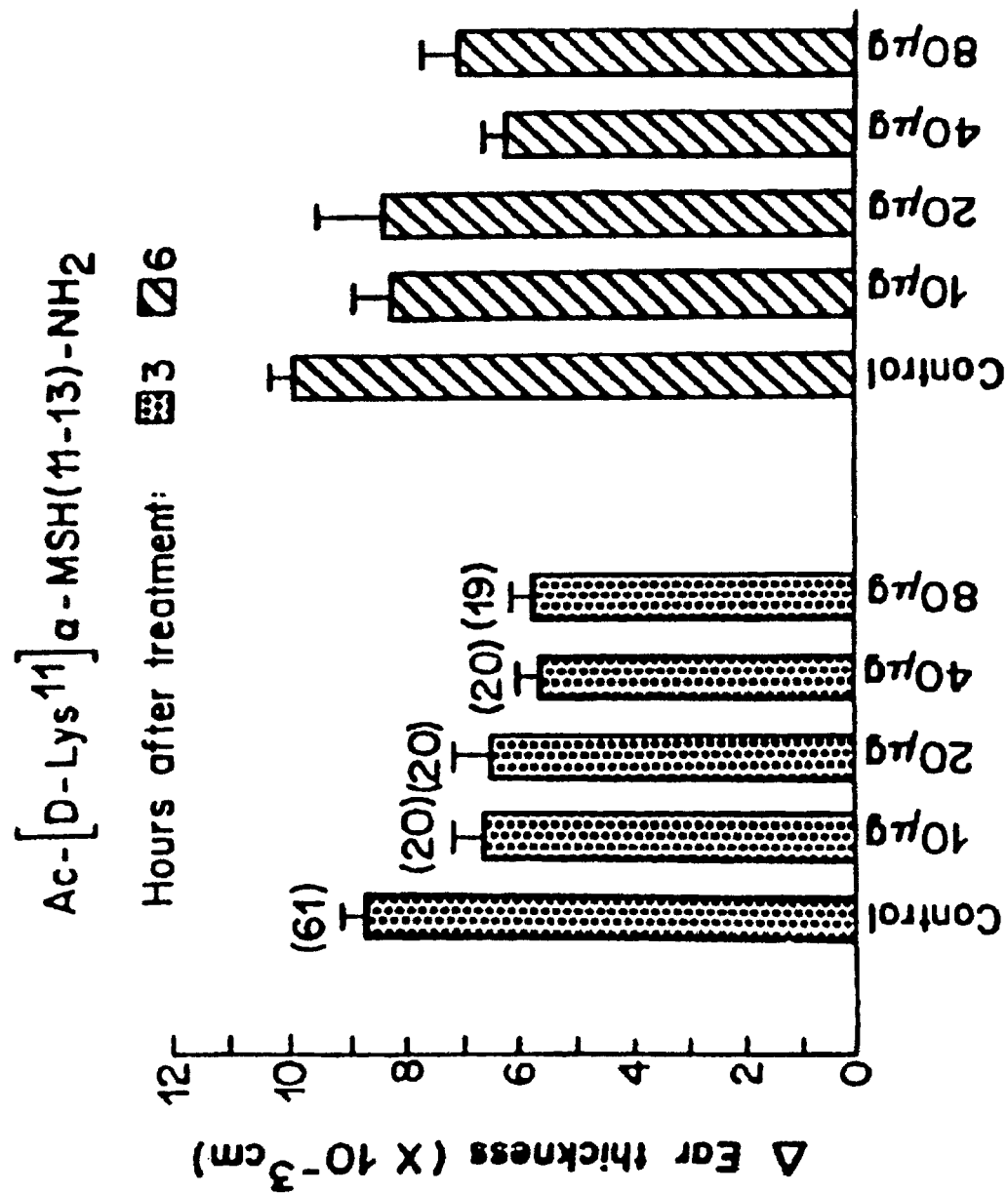

FIG. 9 illustrates inhibition of inflammation by Ac-[D-Lys$^{11}$]α-MSH (11–13)-NH$_2$. Scores are mean±SEM differences from baseline measures for control and peptide treatments. Number of animals shown in parentheses.

Figure 10:
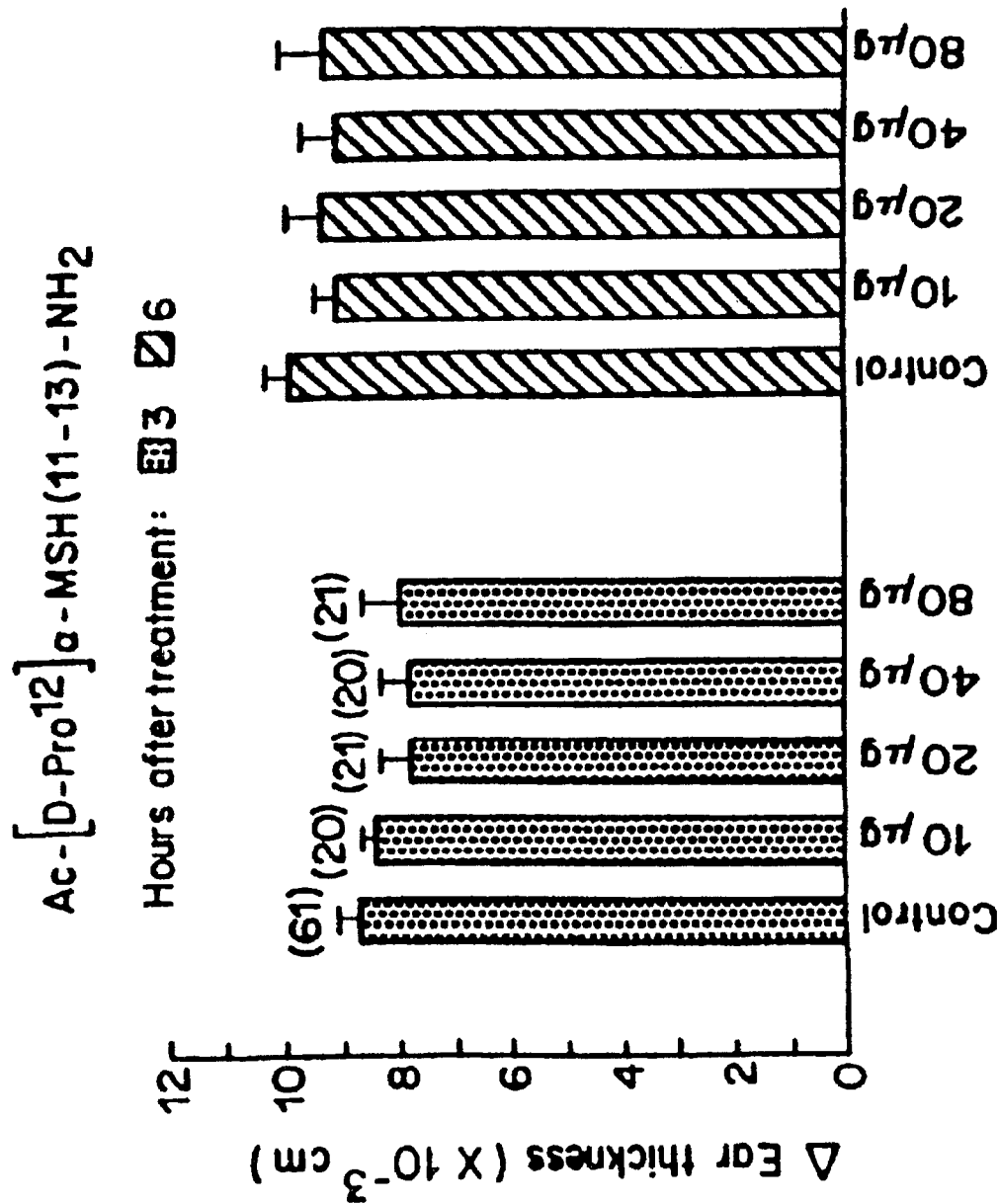

FIG. 10 illustrates the lack of inflammation by Ac-[D-Pro$^{12}$]α-MSH (11–13)-NH$_2$. Scores are mean±SEM differences from baseline measures for control and peptide treatments. Number of animals shown in parentheses.

Figure 11:
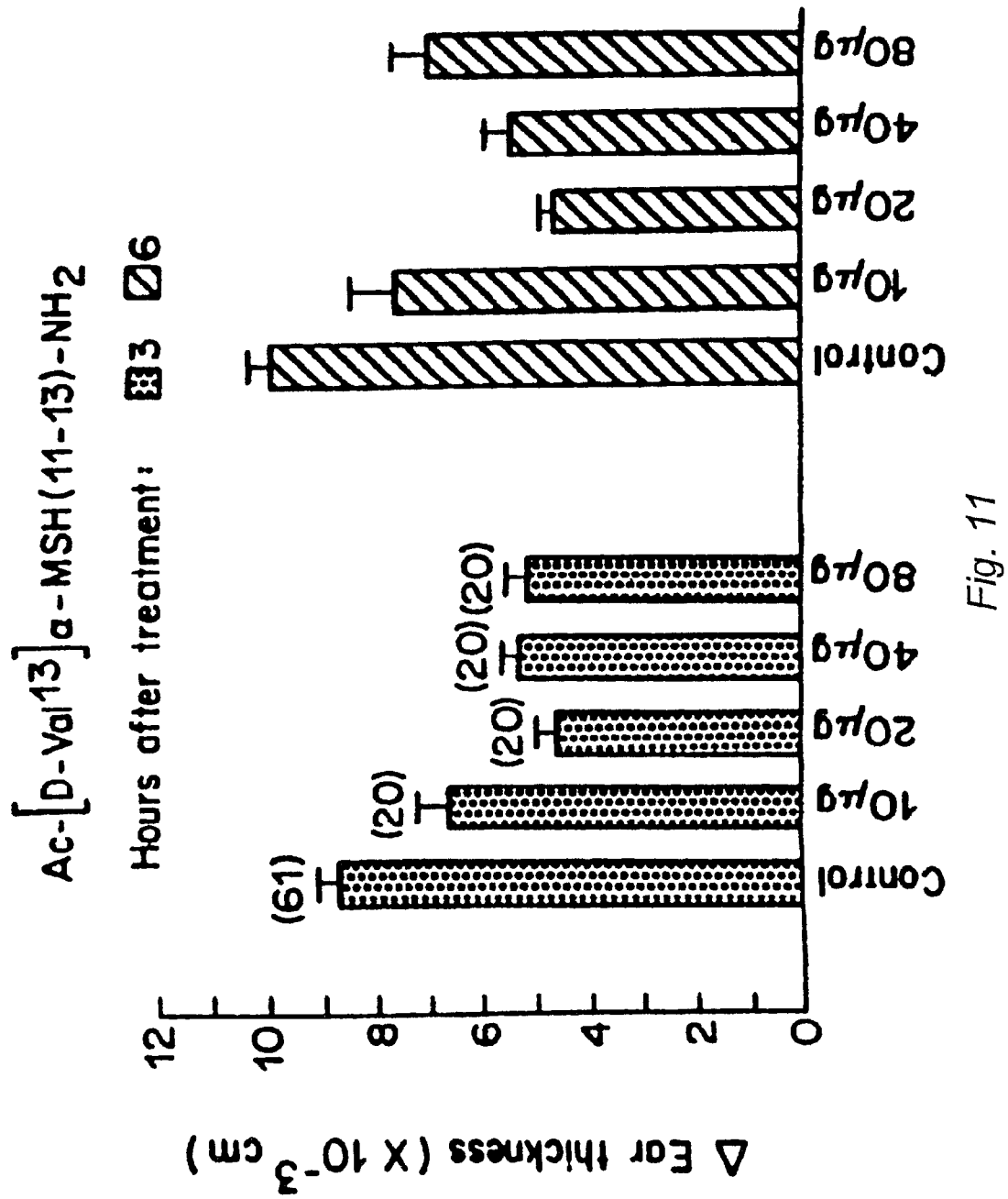

FIG. 11 illustrates the inhibition of inflammation by Ac[D-Val$^{13}$]α-MSH (11–13)-NH$_2$. Scores are mean±SEM differences from baseline measures for control and peptide treatments. Number of animals shown in parentheses.

Figure 12:
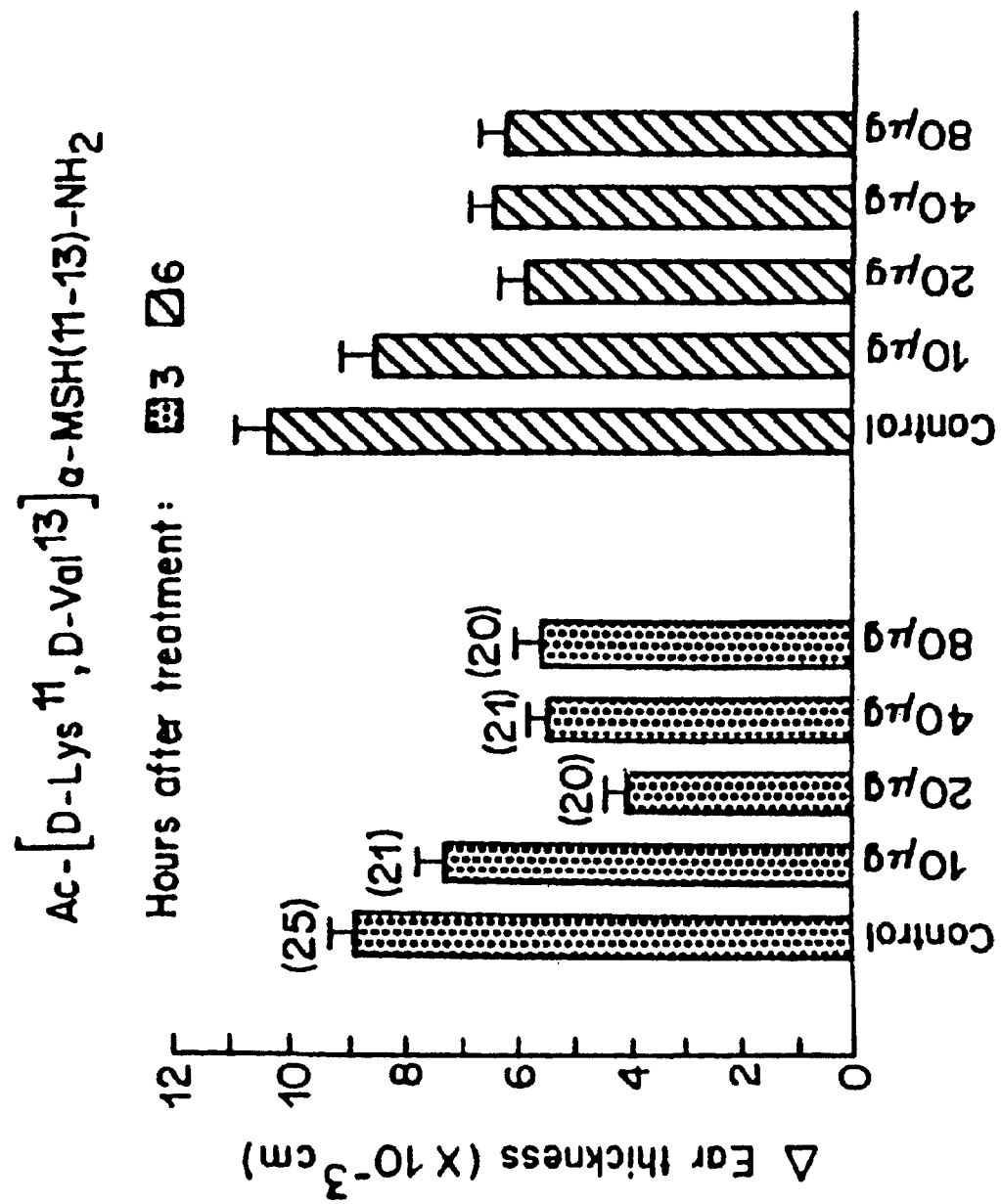

FIG. 12 illustrates inhibition of inflammation by Ac-[D-Lys$^{11}$, D-Val$^{13}$]α-MSH (11–13)-NH$_2$. Scores are mean±SEM differences from baseline measures for control and peptide treatments. Number of animals shown in parentheses.

Figure 13:
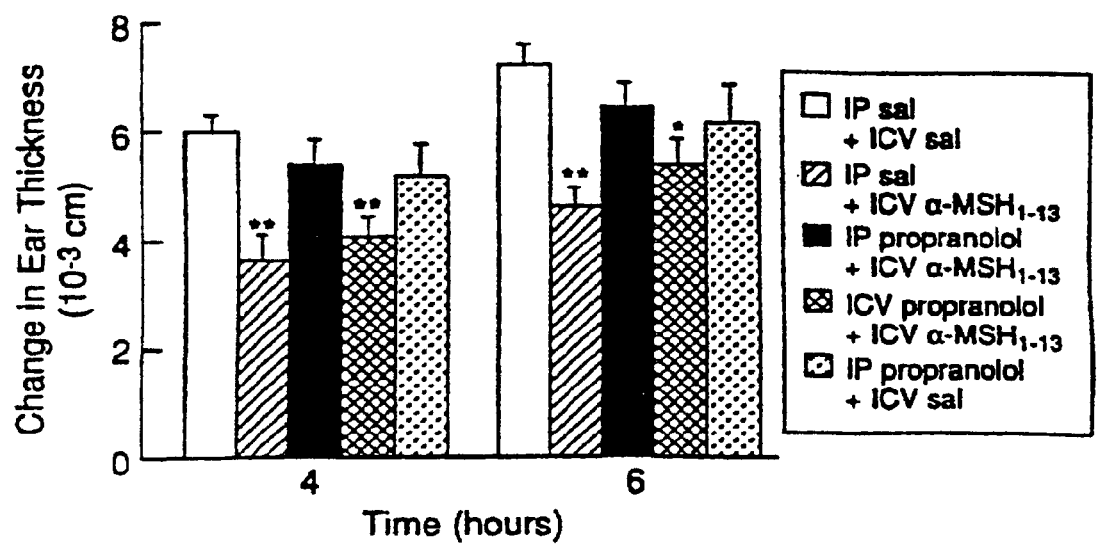

FIG. 13 illustrates the relative inhibition of α-MSH (11–13)'s anti-inflammatory action on edema caused by intradernal injection of human recombinant 1L1β in the mouse ear. "IP" refers to intraperitoneal injection. "Sal" refers to a saline solution. "ICV" refers to an intracerebroventricular injection.

Figure 14:
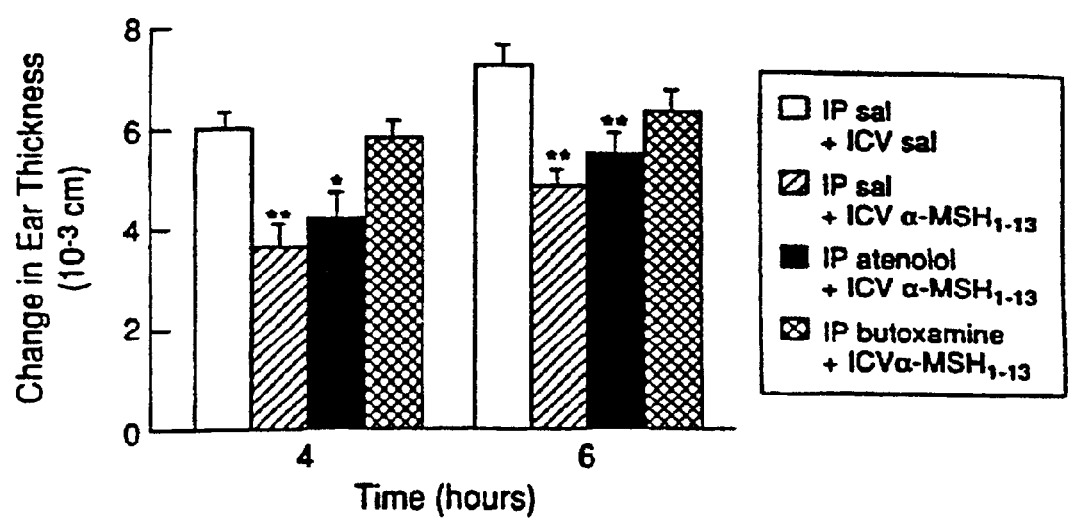

FIG. 14 illustrates the relative inhibition of the anti-inflammatory actions of centrally administered α-MSH (11–13) by β$_2$-adrenergic antagonist butoxamine. Atenolol is a β$_1$- adrenergic antagonist.

Figure 15:
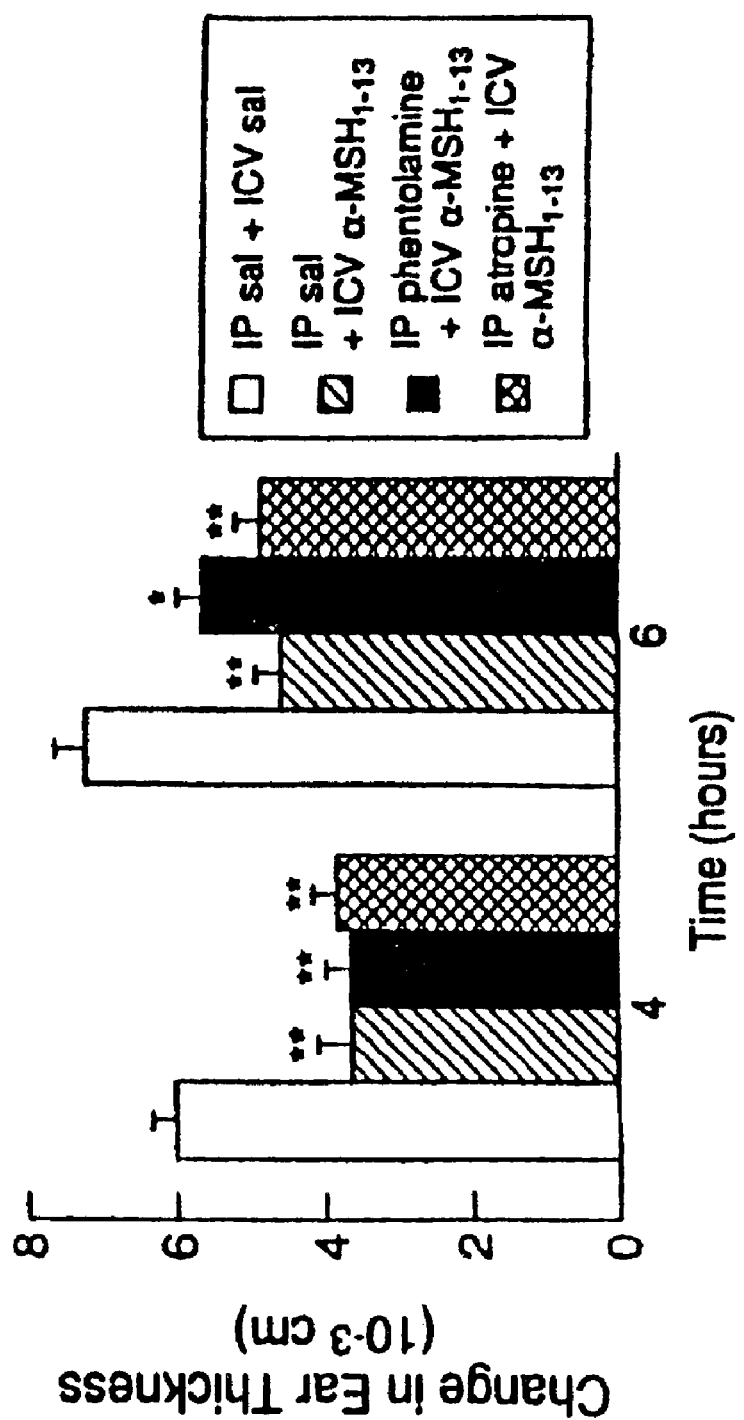

FIG. 15 illustrates the relative inhibition of the anti-inflammatory actions of centrally administered α-MSH (11–13) in the presence of an α-receptor antagonist. Phentolamine is a cholinergic receptor antagonist.

Figure 16:
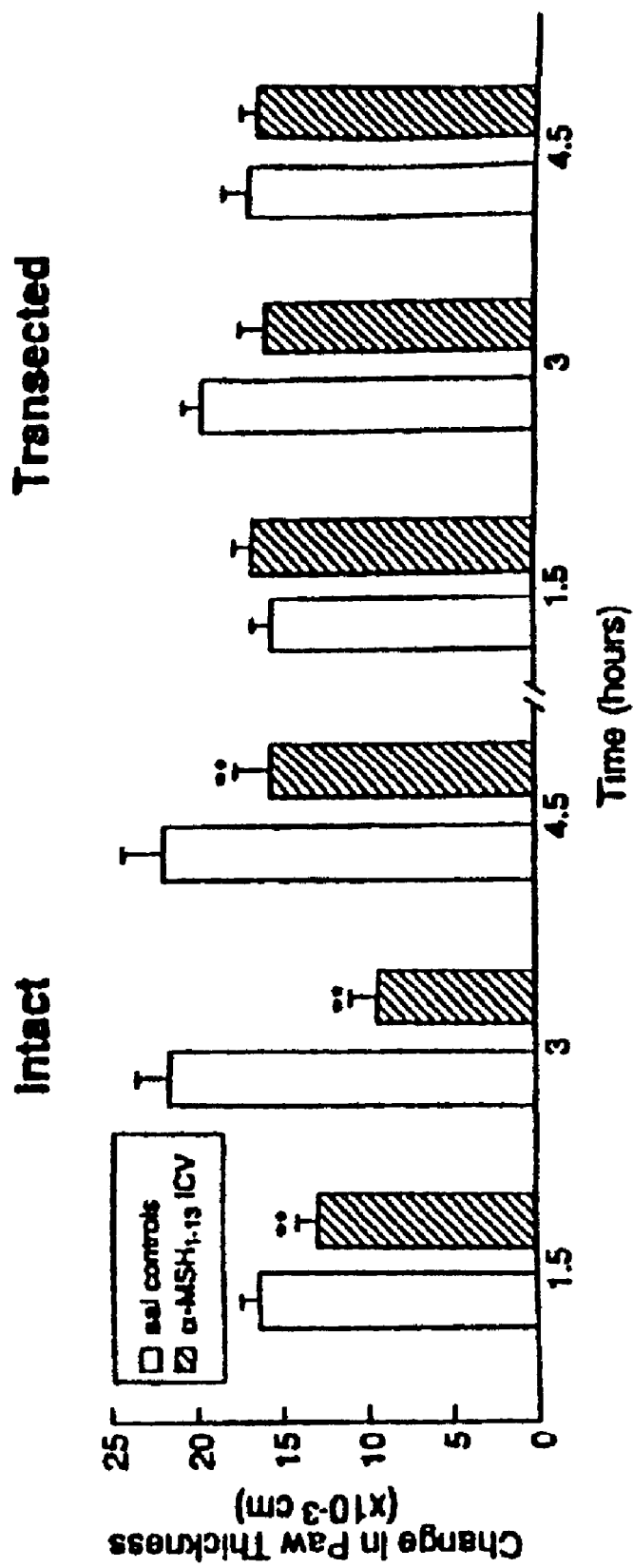

FIG. 16 illustrates the relative inhibition of the anti-inflammatory actions of centrally administered α-MSH (11–13) as a function of time in spinal cord transected mice.

Figure 17:
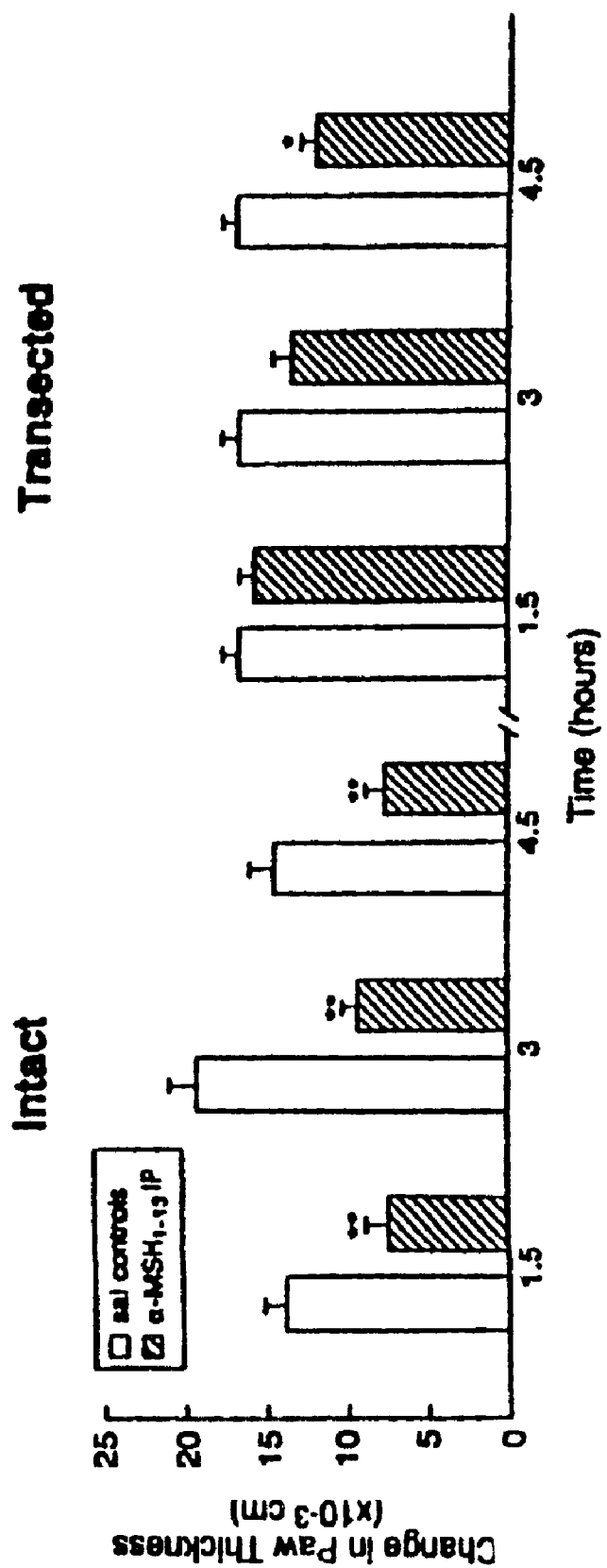

FIG. 17 illustrates the relative inhibition of the anti-inflammatory actions of systemically administered α-MSH (11–13) as a function time in spinal cord transected mice.

Figure 18:
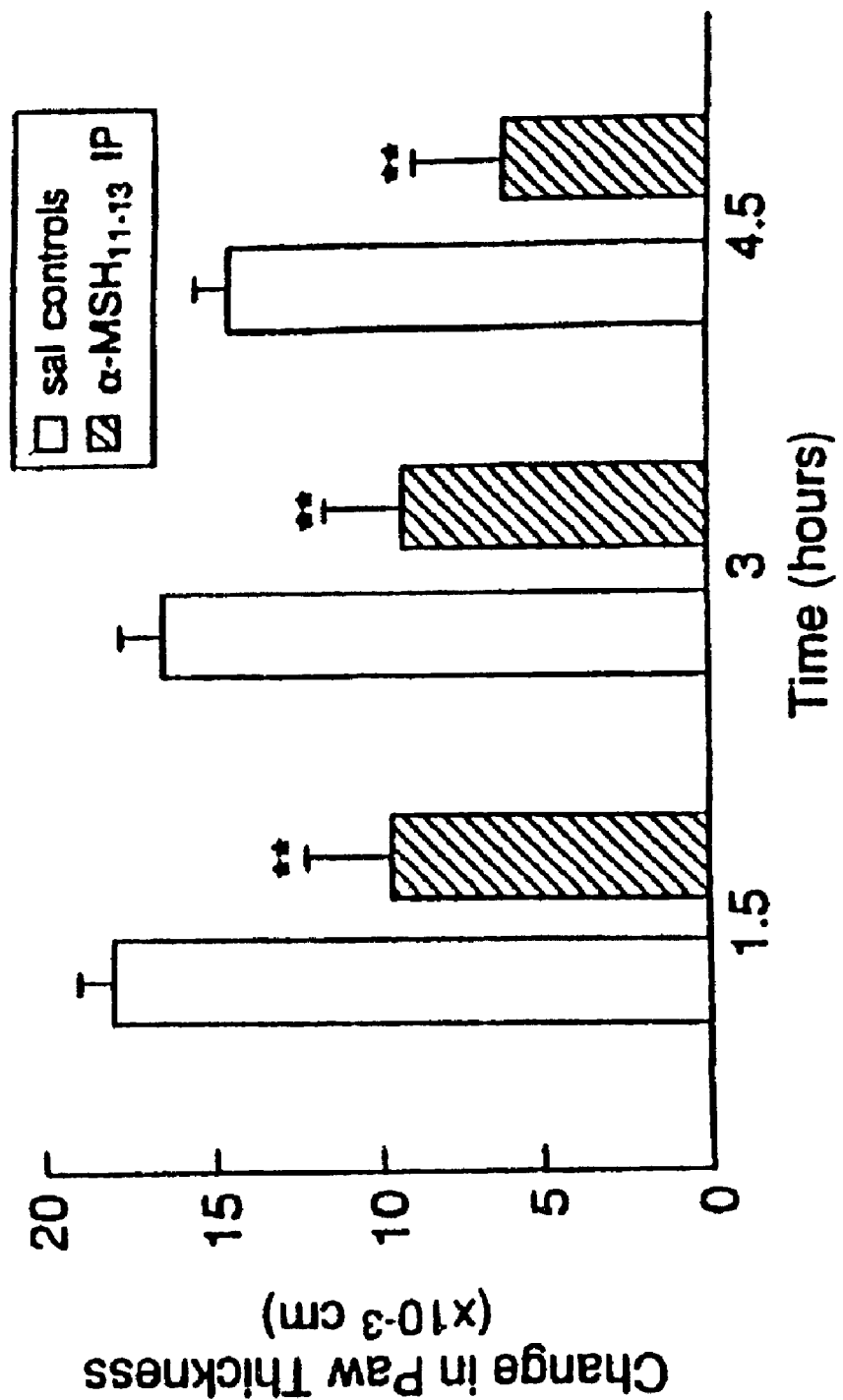

FIG. 18 illustrates the relative inhibition of the anti-inflammatory actions of systemically administered α-MSH (11–13) as a function time in spinal cord transected mice.

Figure 19:
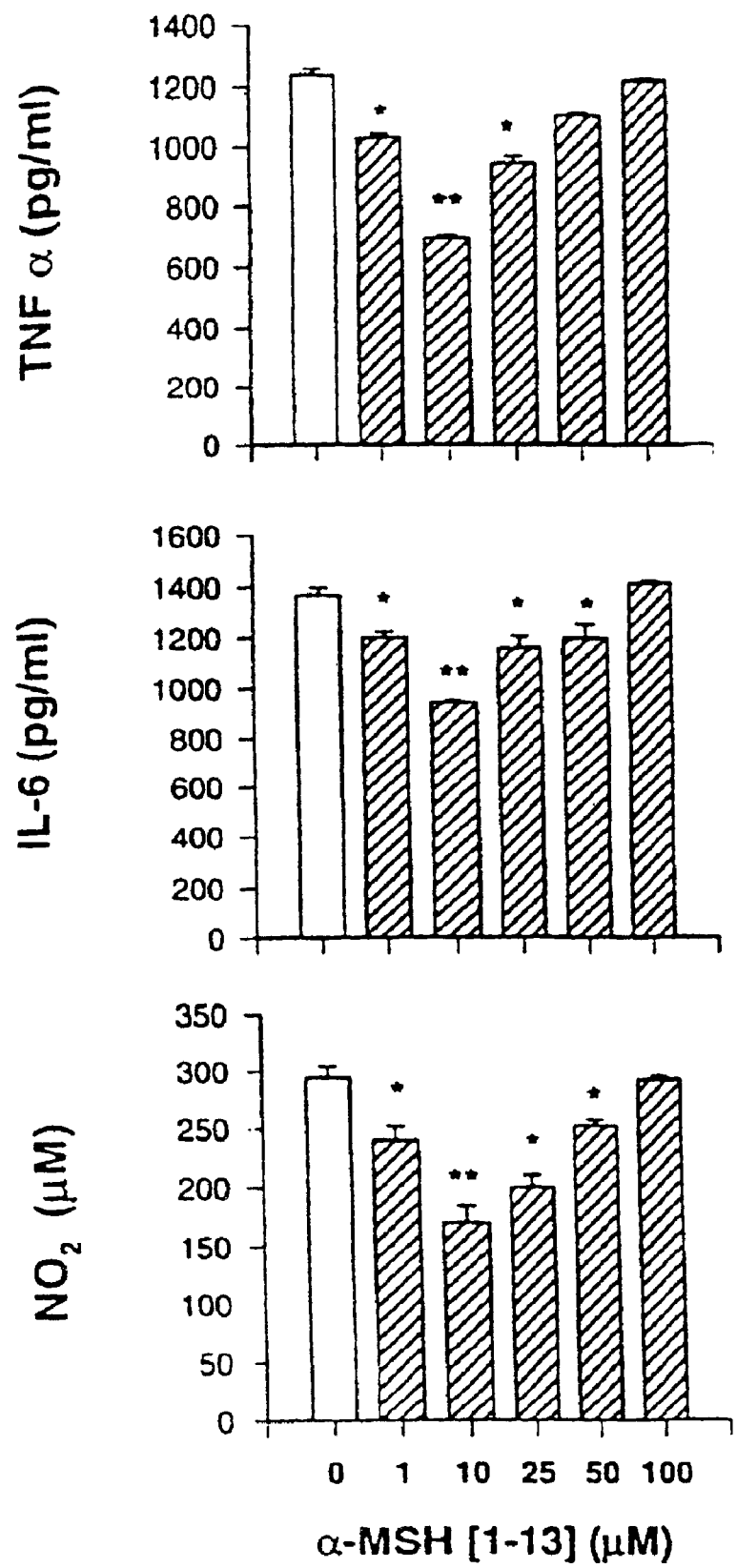

FIG. 19 shows the relative change in concentrations of $NO^-_2$, IL-6 and TNF-α as a function of α-MSH (11–13) concentration in activated microglia.

Figure 20:
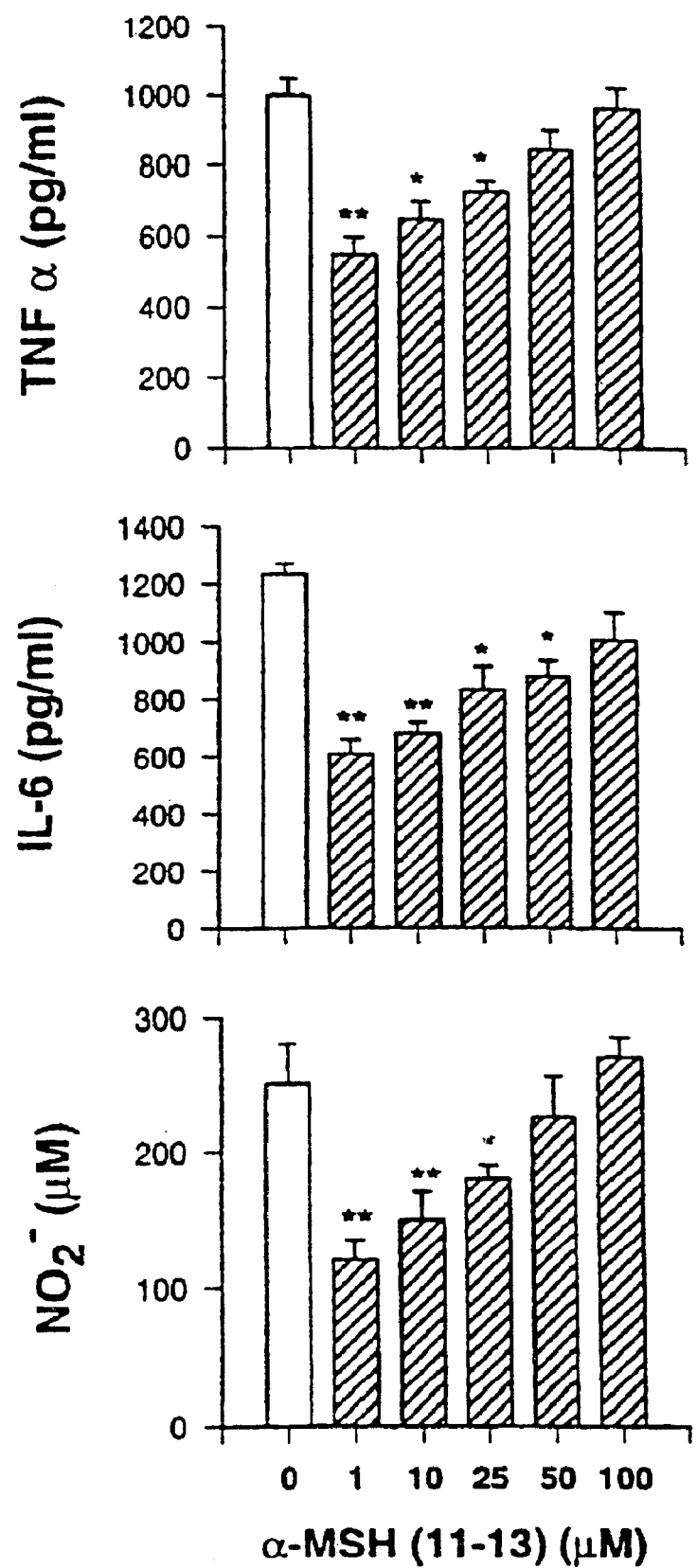

FIG. 20 shows the relative change in concentrations of $NO^-_2$, IL-6 and TNF-α as a function of α-MSH (1–13) concentration in activated microglia.

Figure 21:
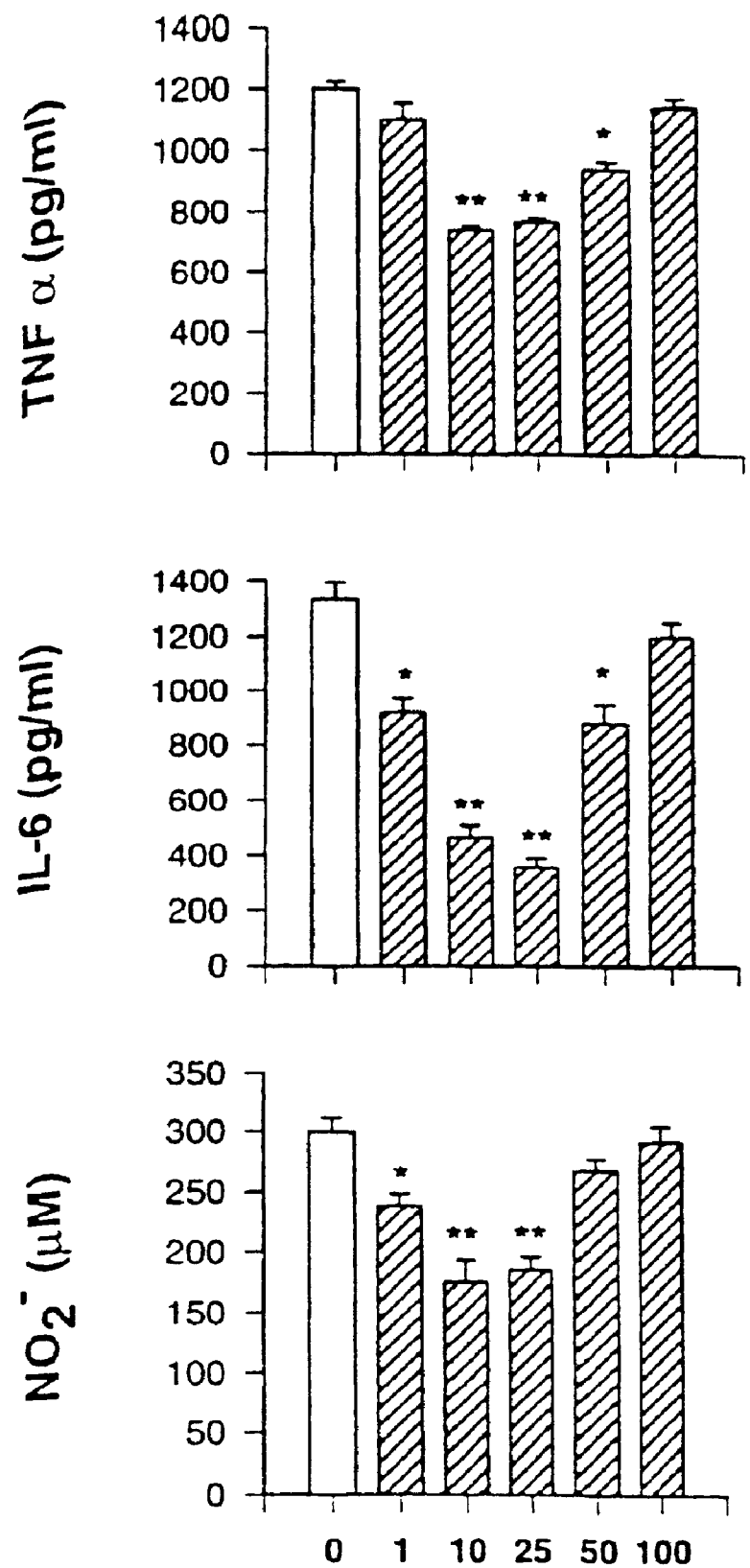

FIG. 21 shows the relative change in concentrations of $NO^-_2$, IL-6 and TNF-α as a function of ACTH (1–24) concentration in activated microglia.

Figure 22:
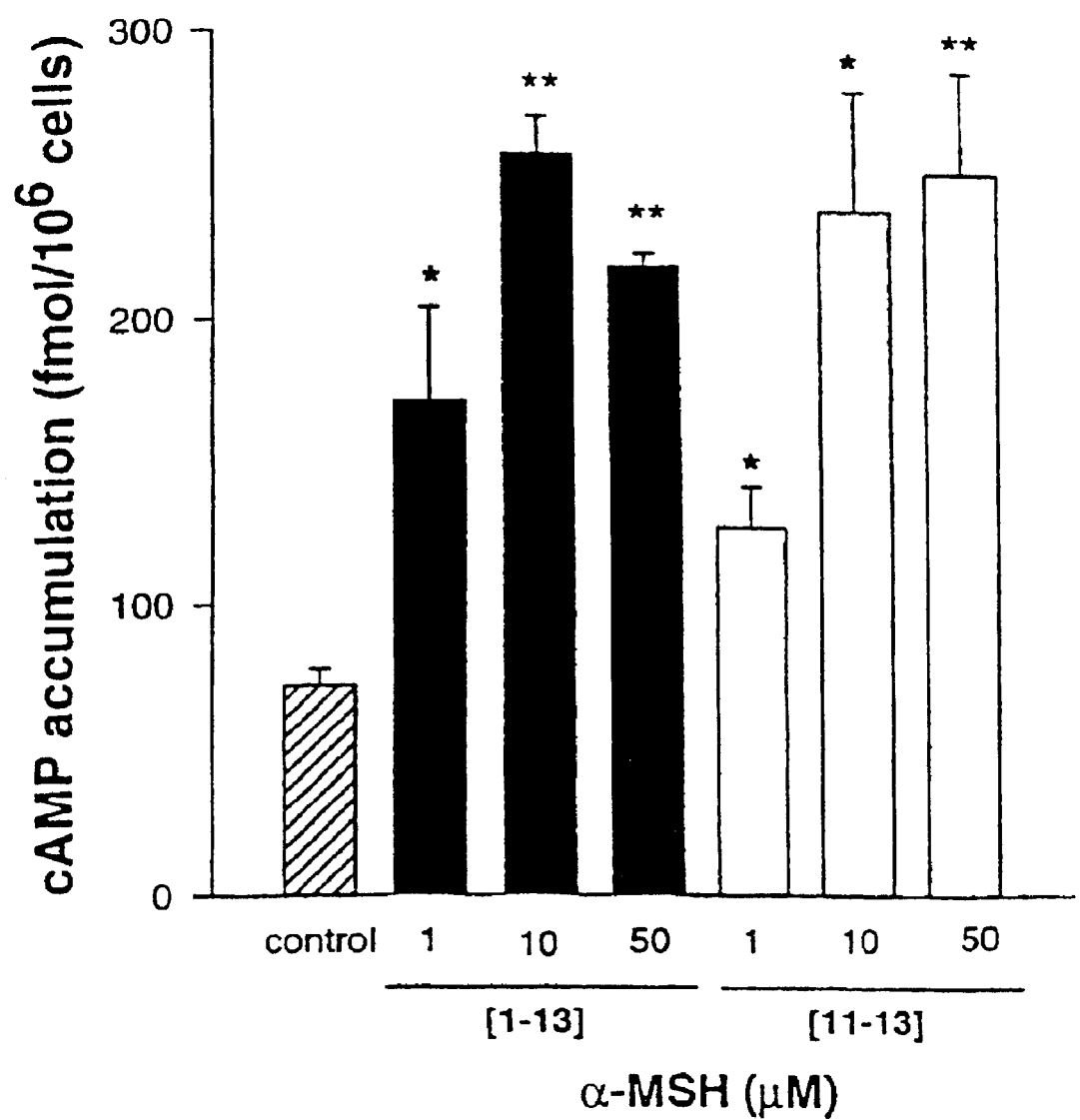

FIG. 22 shows the relative accumulation of cAMP as a function of α-MSH (1–13) and α-MSH (11–13) concentration in resting microglia.

Figure 23:
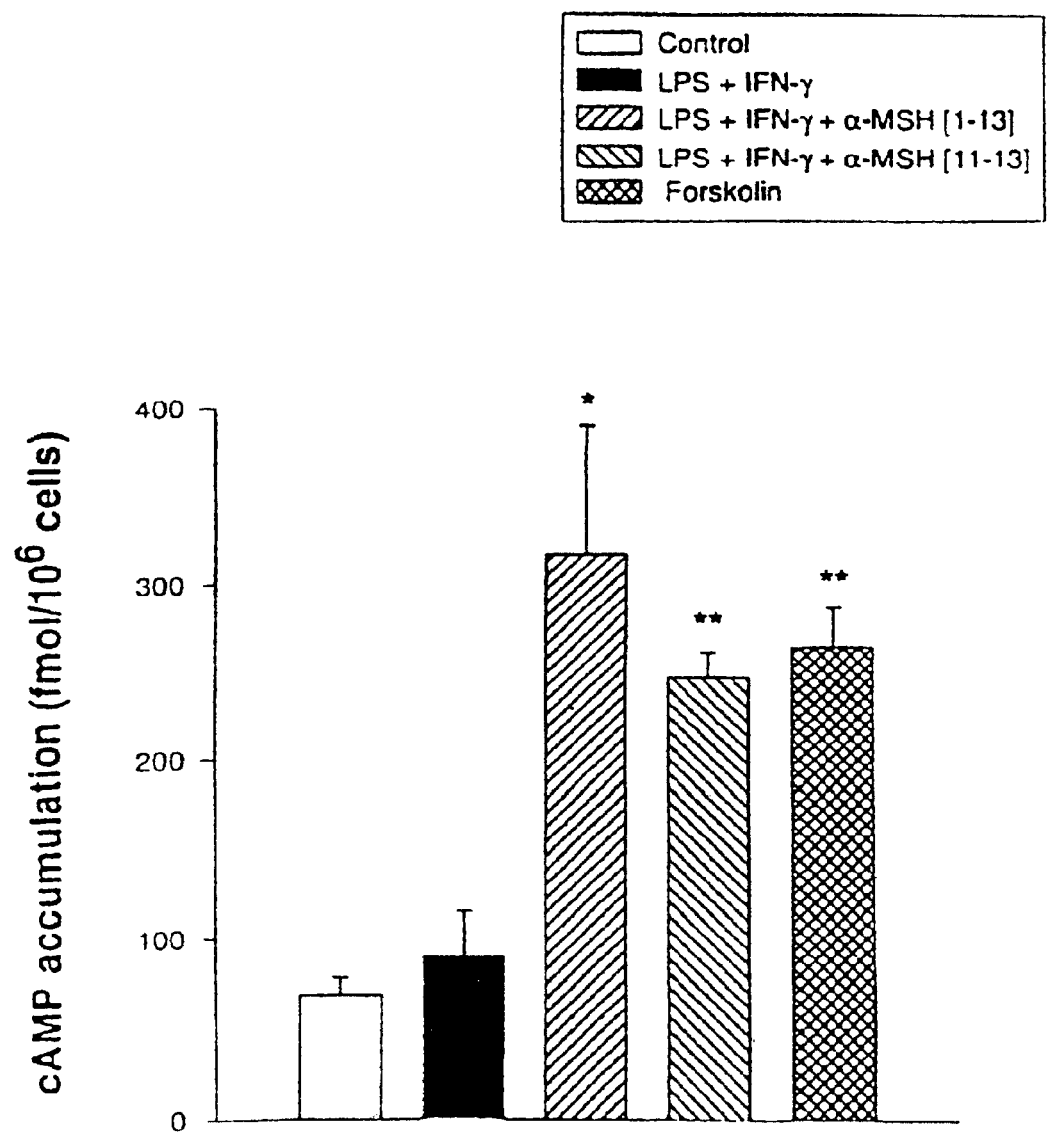

FIG. 23 shows the relative change in concentrations of $NO^-_2$, IL-6 and TNF-α as a function of α-MSH (11–13) microglia co-incubated with LPS+IFN-α.

Figure 24:
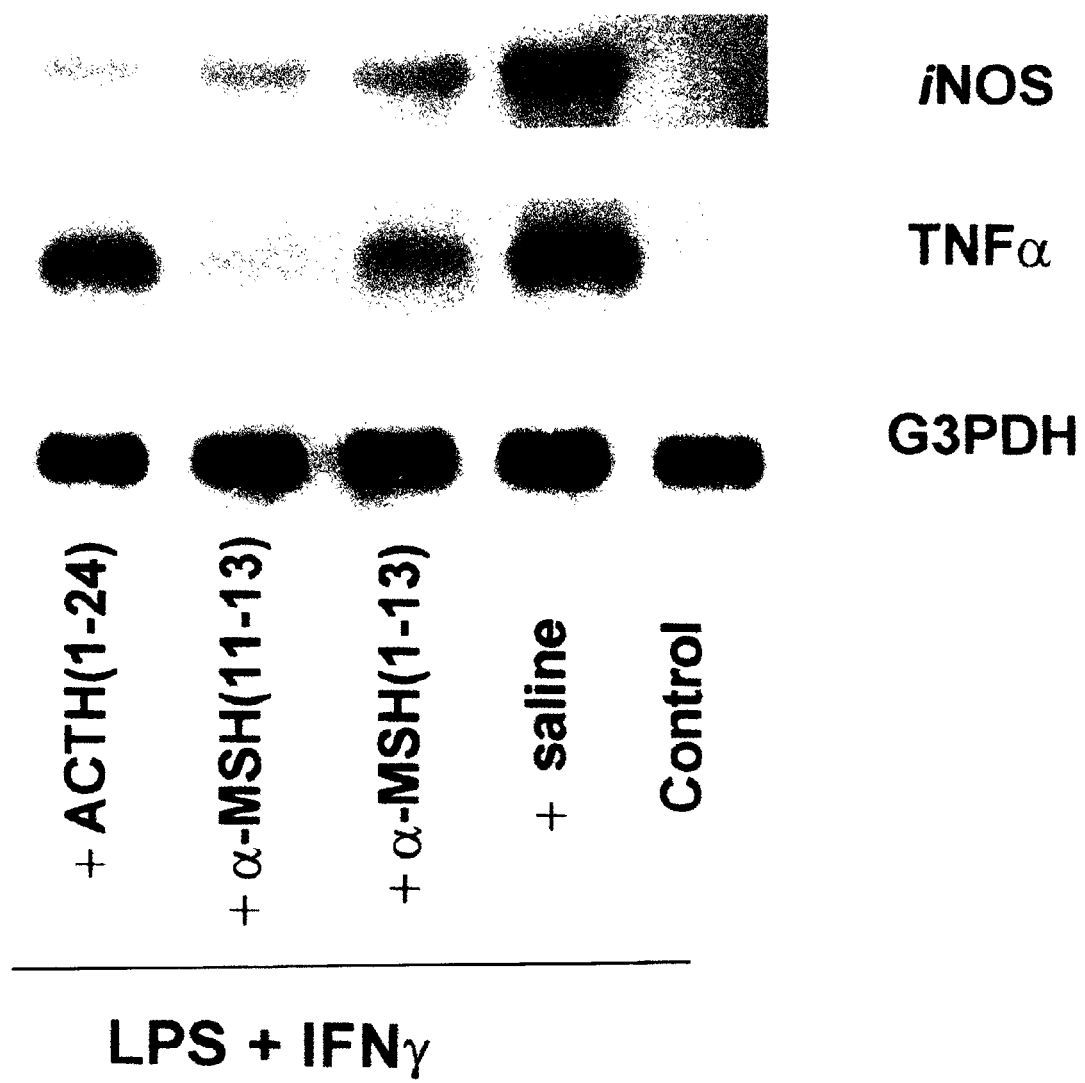

FIG. 24 is a Northern Blot showing the inhibitory influences of melanocortin peptides ACTH (1–24), α-MSH (1–13), α-MSH (11–13)) on TNF-α and $NO^-_2$ production in activated microglia.

Figure 25:
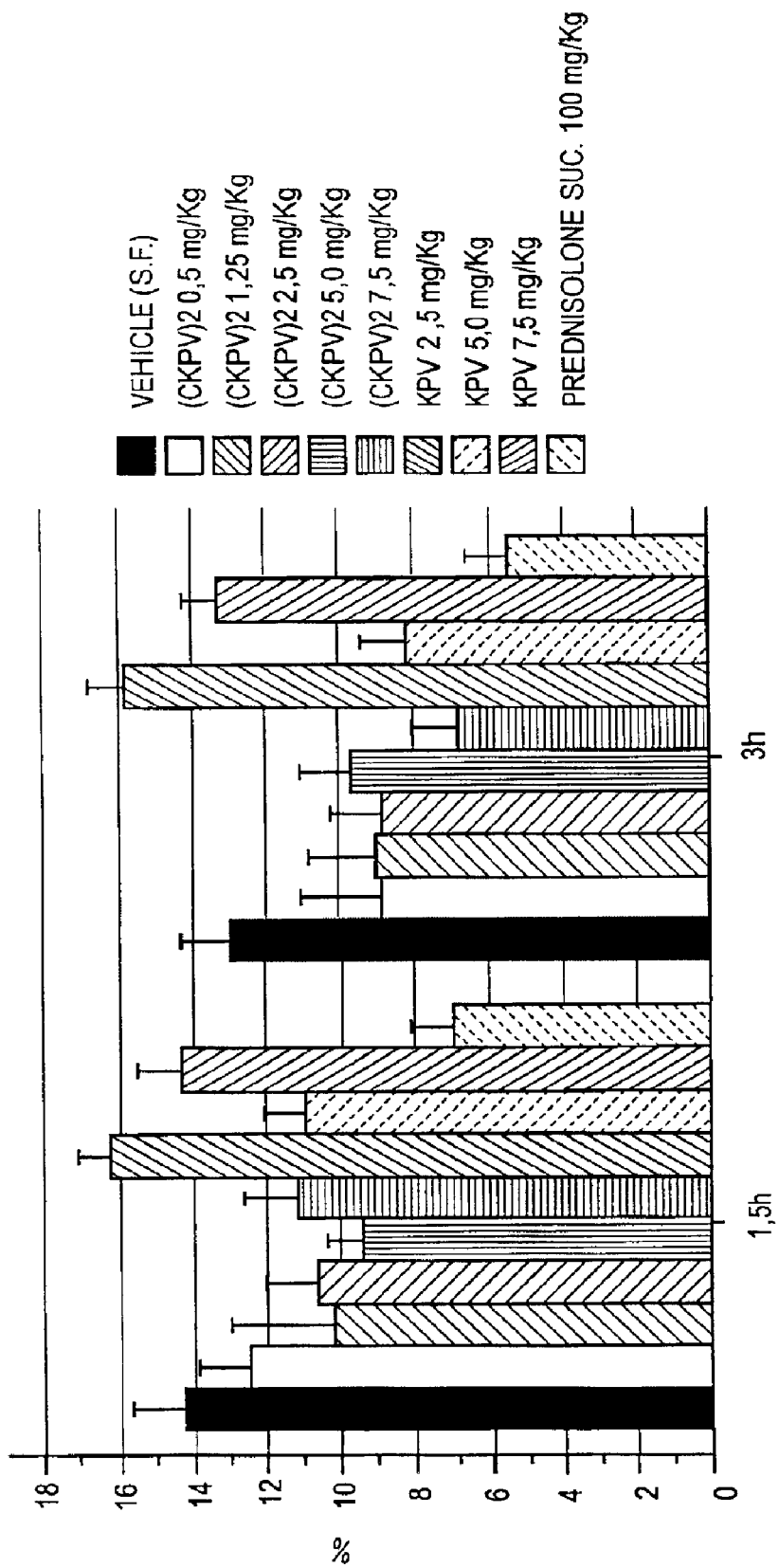

FIG. 25 illustrates the anti-inflammatory effects of the KPV (SEQ ID NO:1) peptide, KPV (SEQ ID NO:1) dimer and prednisolone on edema induced in the hind paw of mice by the injection α-carageenan as a function of time.

Figure 26:
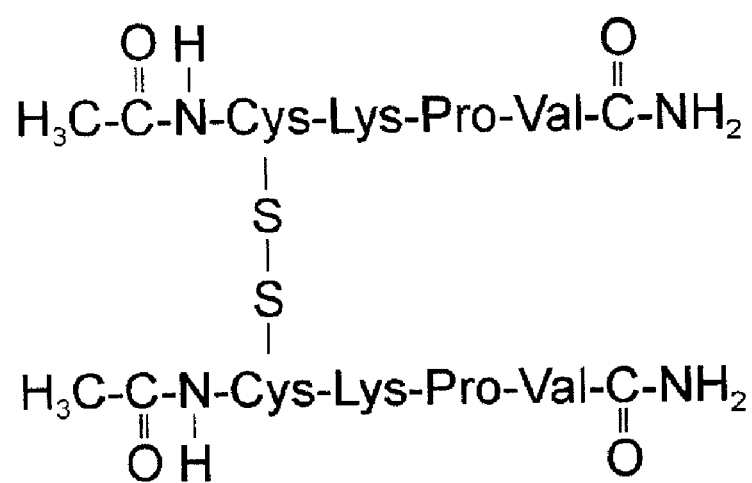

FIG. 26 illustrates a representation of the chemical structure of one form of the KPV (SEQ ID NO:1) dimer for use with one aspect of the invention.

Table 1 shows the relative reduction in histamine induced blue weal formation as a function of α-MSH (11–13) dosage.

Table 2 shows the anti-inflammatory activity of substituted α-MSH peptides. An anti-inflammatory activity is expressed as percent inhibition of swelling.

GENERAL DESCRIPTION OF THE INVENTION

The references cited above and below are incorporated by reference as if fully set forth herein. The present invention involves a composition and a method for treatment for animal pruritus utilizing α-MSH and/or its derivatives.

α-MSH is a 13 amino acid with the primary sequence SYSMEHFRWGKPV (SEQ ID NO:4). In addition to anti-inflanunatory properties, antibiotic and its anti-fungal properties, it also has anti-pyretic properties. The C-terminal tripeptide, KPV (SEQ ID NO:1), appears responsible for these properties. Lipton, J. M., *Antipyretic and Anti-inflammatory Lys-Pro-Val-Compositions and Methods of Use,* U.S. Pat. No. 5,028,592, issued Jul. 2, 1991; Lipton, J. M., *Antipyretic and Anti-inflammatory Lys-Pro-Val-Compositions and Methods of Use,* U.S. Pat. No. 5,157,023, issued Oct. 20, 1992; Catania, A., Lipton J. M., *α-Melanocyte Stimulating Hormone in the Modulation of Host Reactions,* 14 Endocr. Rev., 564–576 (1993); Lipton, J. M., Catania, A., *Anti-inflammatory Influence of the Neuroimmunomodulator α-MSH,* 18 Imniunol. Today, 140–145 (1997).

The core α-MSH sequence (4–10) has learning, memory and behavioral effects but limited anti-pyretic and anti-inflammatory activity. Lipton, J. M., Catania, A., *Anti-inflammatory Influence of the Neuroimmunomodulator α-MSH,* 18 Immunol. Today, 140–145 (1997). α-MSH, the α-MSH core and its tripeptide C-terminal have very low toxicity. Id.

α-MSH is produced by the post-translational processing of propriomelanocortin and shares the 1–13 primary sequence with adrenocortitrophic hormone (ACTH). Eberle, A. N., *The Melanotropins,* Karger, Basel, Switzerland (1988). It is secreted by a wide variety of cell types, including pituitary cells, monocytes, melanocytes, keratinocytes, epidermal cells and the epithelial cells of mucous membranes. Lipton, J. M., Catania, A., *Anti-inflammatory Influence of the Neuroimmunomodulator α-MSH,* 18 Immunol. Today, 140–145 (1997).

α-MSH reduces inflammation by modulating the inflammatory cascade locally and systemically. Rajora, N., Ceriani, G., Catania, A., Star, R. A., Murphy, M. T., Lipton, J. M., *α-MSH Production, Receptors and Influence of Neopterin, in a Human Monocyte/macrophage Cell Line,* 59H. Leukoc. Biol., 248–253 (1996); Star, R. A., Rajora, N. Huang, J., Stock, R. C., Catania, A., Lipton, J. M., *Evidence of Autocrine Modulation of Macrophage Nitric Oxide Synthase by α-MSH,* 92 Proc. Natl. Acad. Sci., 8016–8020 (1995); Lipton, J. M., Ceriani, G., Macaluso, A., McCoy, D., Cames, K., Biltz, J., Catania, A., *Anti-inflammatory Effects of the Neuropeptide α-MSH in Acute, Chronic and Systemic Inflammation,* 741 Ann. N.Y. Acad. Sci., 137–148 (1994); Rajora, N., Boccoli, G., Burns, D., Sharma, S., Catania, A., Lipton, J. M., *α-MSH Modulates Local Circulating Tumor Necrosis Factor A in Experimental Brain Inflammation,* 17 J. Neurosci, 2181–2186 (1997); Richards, D. B., Lipton, J. M. *Effect of α-MSH (11–13) (Lys-Pro-Val) on Fever in Rabbits,* 5 Peptides, 815–817 (1984); Hiltz, M. E., Lipton, J. M., *Anti-inflammatory Activity of a COOH-terminal Fragment of the Neuropeptide α-MSH,* 3 FASEB J., 2282–2284 (1989).

α-MSH (1–13) derivatives are also effective in the treatment of animal pruritus. Derivatives include biologically functional equivalents and hydropathic amino acids, as described in Example I, infra, as well as selected amino acid sequences within the native α-MSH (1–13) chemical structure, i.e. KPV (SEQ ID NO:1), MEHFRWG (SEQ ID NO:2), HFRWGKPV (SEQ ID NO:3).

One aspect of the invention is a composition and method of treatment of animal pruritus having an inflammatory bacterial and/or fungal component. A preferred embodiment of the invention is a composition for the treatment of animal pruritus comprising a therapeutically effective amount of one or more peptides having a C-terminal sequence consisting of KPV (SEQ ID NO:1), MEHFRWG (SEQ ID NO:2), HFRWGKPV (SEQ ID NO:3), and SYSMEHFRWGKPV (SEQ ID NO:4) in combination with a shampoo.

Another preferred embodiment of the invention is a composition for the treatment of animal pruritus comprising a therapeutically effective amount of one or more peptides having a C-terminal sequence consisting of KPV (SEQ ID NO:1), MEHFRWG (SEQ ID NO:2), HFRWGKPV (SEQ ID NO:3), and SYSMEHFRWGKPV (SEQ ID NO:4) in combination with a therapeutically effective amount of a cortisol based glucocorticoid such as betamethasone, cortisone, dexamethasone, hydrocortisone, methyiprednisone, prednisone, and triamcinolone and a shampoo.

Instead of glucocorticoids, a pharmacologically effective amount of non-steroidal anti-inflammatory drugs (NSAID) such as acetylsalicylic acid, diflusinal, fenoprophen calcium, ibuprofen, indomethacin, meclofenamate sodium, naproxen, phenylbutazone, piroxicam, sulindac, and tolmetin sodium may be employed in combination with the preferred peptides.

In another embodiment of the invention each of these compositions may comprise a therapeutically effective amount of an antibiotic such as quinalones, penicillins, lincomides, β-lactam inhibitors, cephalosporins, aminoglycocides, and tetracyclines.

In another embodiment of the invention each of these compositions may further comprise a therapeutically effective amount of an antifunal such as itraconazole, econazole, ketaconazole, miconazole and fluconazole.

More preferably still, the peptides in each of these preferred combination compositions has the primary sequence of KPV (SEQ ID NO:1) or VPK-Ac-CC-Ac-KPV (Ac=Acetyl group). In all the preferred compositions, pharmacologically effective concentrations of the peplides may be as low as $10^{-12}$ M but may be as high $10^{-4}$ M.

In yet another embodiment of the invention, one or one or more peptides having a C-terminal sequence of KPV (SEQ ID NO:1), such KPV (SEQ ID NO:1), MEHFRWG (SEQ ID NO:2), HFRWGKPV (SEQ ID NO:3), and SYSMEHFR-WGKPV (SEQ ID NO:4), which may or may not be in combination with therapeutically effective amounts of antibiotics, corticosteroids, and/or antiflingals is dissolved in a carrier. Formulations for solution or solid based drug delivery carriers are well known in the art. Such preferred carriers include, but are not limited to, saline, phosphate buffered saline, gelatin, maltodextrin, cellulose, microcrystalline cellulose, methyl cellulose and carboxymethyl cellulose.

The formulation of tablets are well known in the art. An exemplary formulation of a hard gelatinous tablet comprises:

| | |
|---|---|
| Gelatine Bloom 30 | 70.0 mg |
| Maltodextrin MD 05 | 108.0 mg |
| di-α-tocopherol | 2.0 mg |
| Sodium ascorbate | 10.0 mg |
| Microcrystalline cellulose | 48.0 mg |
| Magnesium stearate | 2.0 mg |
| α-MSH (11–13) | $.2*10^{-9} - .2*10^{-13}$ mg |

An exemplary formulation of a hard tablet comprises:

| | |
|---|---|
| Anhydrous lactose | 130.5 mg |
| Microcrystalline cellulose | 80.0 mg |
| di-α-tocopherol | 2.0 mg |
| Sodium ascorbate | 10.0 mg |
| Polyvinylpyrrolidone K30 | 5.0 mg |
| Magnesium stearate | 2.0 mg |
| α-MSH (11–13) | $.2*10^{-9} - .2*10^{-13}$ mg |

Alternative carriers include common commercial formulations for shampoos, creams, ointments, balms, aerosol foams, gels or liquids. The carrier itself or a component dissolved in the carrier may have palliative or therapeutic properties of its own, including moisturizing, cleansing, or anti-inflammatory/anti-itching properties.

Formulations of creams and gels are well known in the art. HARRY'S COMSETICOLOGY (Chemical Publishing, 7th ed. 1982); REMINGTON'S PHARMACEUTICAL SCIENCES (Mack Publishing Co., 18th ed. 1990).

By far, the most common cleansing agent used in the treatment of animals is a shampoo. Set forth below are examples of various formulations of the invention in different classifications of shampoos. Examples of some systemic preparations are also included showing the invention in those formulations. As used below the term "Active Ingredient" refers to one or more peptides having a C-terminal sequence of KPV (SEQ ID NO:1), such KPV (SEQ ID NO:1), MEHFRWG (SEQ ID NO:2), HFRWGKPV (SEQ ID NO:3), and SYSMEHFRWGKPV (SEQ ID NO:4). Preferably, the active ingredient is KPV (SEQ ID NO:1) or VPK-Ac-CC-Ac-KPV.

An exemplary formulation of a clear liquid shampoo based on the invention follows. (In these formulations, the designation of q.s. is meant to refer to a "quantity sufficient" for the desired effect.)

| | |
|---|---|
| Lauryl amino propionic acid | 10% |
| Triethanolamine lauryl sulfate (30–33%) | 25% |
| Coconut diethanolamide | 2.5% |
| Lactic acid to give pH 4.5–5.0 | q.s. |
| Preservative | q.s. |
| Fragrance, color, deionized water | up to 100% |
| α-MSH (11–13) | 1 part for 1% to 5 parts for 5% solution |

An exemplary formulation of a moisturizing shampoo based on the invention comprises:

| | |
|---|---|
| Triethanolamine lauryl sulphate (30–33%) | 49% |
| Triethanolamine oleate (50%) | 9.8% |
| Propylene glycol | 2% |
| Oleyl alcohol | 1.0% |
| Water | 38.2% |
| α-MSH (11–13) | 1 part for 1% to 5 parts for 5% solution |

Another exemplary formulation of a liquid cream or lotion shampoo based on the invention, comprises:

| | |
|---|---|
| Sodium lauryl sulphate | 25% |
| Polyethylene Glycol 400 distearate | 5% |
| Magnesium stearate | 2.0% |
| Distilled water | 68% |
| Fatty acid alkanolamide (for thickening) | q.s. |
| Oleyl alcohol (for conditioning) | q.s. |
| α-MSH (11–13) | 1 part for 1% to 5 parts for 5% solution |

Another exemplary formulation or a solid cream or gel shampoo based on the invention comprises:

| | |
|---|---|
| Sodium lauryl sulfate (100%) | 20% |
| Coconut monoethanolamide | 1.0% |
| Propyleneglycol monostearate | 2.0% |
| Stearic acid | 5.0% |
| Sodium hydroxide | .75% |
| Water, perfume, color if desired | up to 100% |
| α-MSH (11–13) | 1 part for 1% to 5 parts for 5% solution |

An exemplary formulation of an oil shampoo based on the invention comprises:

| | |
|---|---|
| Sulphonated olive oil | 16.0% |
| Sulphonated castor oil | 16.0% |
| Water | 68.0% |
| Color, perfume | q.s. |
| α-MSH (11–13) | 1 part for 1% to 5 parts for 5% solution |

Certain pruritic conditions are caused by drainage from an exposed wound or injury. In such a case, a dry shampoo based on the invention would be preferable. An exemplary formulation of a dry shampoo based on the invention comprises:

| | |
|---|---|
| Insoluble rice starch (tetramethyl acetylendiurea reaction product) | 30.0% |
| Boric acid | 7.0% |
| Finely divided silica | 25.0% |
| Starch | 23.0% |
| Talc | 15.0% |
| Perfume Oil | q.s. |
| α-MSH (11–13) | 1 part for 1% to 5 parts for 5% solution |

Another preferred embodiment of the invention is a treatment packet with a wipe made of absorbent material that is treated with α-MSH and/or its derivatives that have been dissolved into a liquid-based carrier. This type of application would be most beneficial in those animals showing some level of alopecia (hair loss), or animals that have been intentionally shaved in localized areas of dermatologic involvement.

The process for making wipes of absorbent material is well known in the art. For example, baby wipes, moist towelettes, make-up removal cloths, and alcohol swabs are all wipes of absorbent material. Commercial examples of such wipes include Chubs® Baby Soft Wipes, Dexus® Antibacterial Hand Wipes, Dexus® Makeup Remover Wipes, Tinactin® Sports Wipes for Athlete's Foot, and B-D® Alcohol Swabs. Treatment of the wipe's absorbent material is accomplished by first soaking the absorbent material in a solution of α-MSH and/or its derivatives. The wipe remains in a liquid-impermeable packaging until use, when the package is opened and the wet wipe is applied to the affected portion of the integument.

The processes for making liquid-impermeable packages are well known in the art. For example, packages made of layers of paper, metal foil, and metal foil coated paper are commonly used for packaging wipes of absorbent material. For example, moist towelettes, such as Massengill® Feminine Cleansing Soft Cloth Towelettes, and alcohol swabs, such as B-D® Alcohol Swabs, are packaged in this manner.

In another embodiment of the invention, α-MSH, and/or its derivatives, may be administered parenterally. Preferred compositions for parenteral administration may be formed by combining the preferred peptides in combination with pharmaceutically acceptable buffers, dilutents and stabilizers. In a preferred composition, approximately 100–500 mg of the preferred peptides is mixed with about 1–7 ml of saline, including a pharmacologically acceptable buffer to maintain a neutral pH.

An exemplary parenteral preparation comprises:

| | |
|---|---|
| Sterile Isotonic Saline | 1–7 cc |
| Pharmaceutically Accepted Buffer | In an amount adequate to maintain pH of about neutral |
| α-MSH (11–13) | 100–500 mg |

Another preferred embodiment of the invention is a method for treating animal pruritis comprising systememic or topical application of a therapeutically effective level of α-MSH, one or more peptides with a C-terminal sequence of KPV (SEQ ID NO:1) such as KPV (SEQ ID NO:1), and HFRWGKPV (SEQ ID NO:3). The peptides of this preferred method may be combined with a shampoo or therapeutically effective amounts of anti-inflammatories such as corticosteroids, fungicides, antibiotics, moisturizers or anti-itching compounds.

Topical administration preferably comprises direct topical application of a pharmacologically effective amount of one or more of the preferred peptides contained in a carrier to the affected regions. A preferred method comprises topical application of a shampoo, a moisturizer, or a moisturizing swab containing pharmacologically effective amounts of one or more of the preferred peptides. Alternatively, topical administration of a pharmacologically effective amount may utilize transdermal delivery systems well known in the art.

Systemic administration preferably comprises ingestion of any solid or solution carriers containing a pharmacologically effective amount of one or more of the preferred peptides. Such solid or solution carriers may comprise pills, hard tablets, soft tablets, gums or ordinary liquids. Additionally, systemic administration of a pharmacologically effective amount may comprise invasive methodologies including intravenous, subcutaneous, intramuscular or intralesional injection of a suitable carrier, such as saline, containing a pharmacologically effective amount of one or more of the preferred peptides.

The following examples demonstrate the application of α-MSH and/or its derivatives.

EXAMPLE I

α-MSH Derivatives

Derivatives of α-MSH are not limited to the native sequence polypeptides within the α-MSH (1–13) chemical structure. This example illustrates the biological functional equivalents of α-MSH. Although specific amino acid sequences described here are effective, it is clear to those familiar with the art that amino acids can be substituted or deleted without altering the effectiveness of the peptides. Further, it is known that stabilization of the α-MSH sequence can greatly increase the activity of the peptide and that substitution of D-amino acid forms for L-forms can improve or decrease the effectiveness of the peptides. For example, a stable analog of α-MSH, [Nle$^4$, D-Phe$^7$]-α-MSH, which is known to have marked biological activity on melanocytes and melanoma cells, is approximately ten times more potent than the parent peptide in reducing fever. Further, adding amino acids to the N-terminal of α-MSH (11–13) sequence can reduce or enhance antipyretic potency. Addition of glycine to form the 10–13 sequence, slightly decreased potency; the 9–13 sequence was almost devoid of activity, whereas the potency of the 8–13 sequence was greater than that of the 11–13 sequence. It is known that Ac-[D-K11]-α-MSH 11–13-NH2 has the same general potency as the L-form of the tripeptide α-MSH (11–13). However, substitution with D-proline in position 12 of the tripeptide rendered it inactive. see e.g. Holdeman, M., et. al., *Antipyretic Activity of a Potent α-MSH Analog,* Peptides 6, 273–5 (1985). Deeter, L. B., et. al., *Antipyretic Properties of Centrally Administered α-MSH Fragments in the Rabbits* Peptides 9, 1285–8 (1989). Hiltz, M. E., *Anti-inflammatory Activity of α-MSH (11–13) Analogs: Influences of Alterations in Stereochemistry,* Peptides 12, 767–71 (1991).

Biological functional equivalents can also be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid. See U.S. Pat. No. 5, 157,023 issued to James M. Lipton issued on Oct. 20, 1992.

Figure 1:
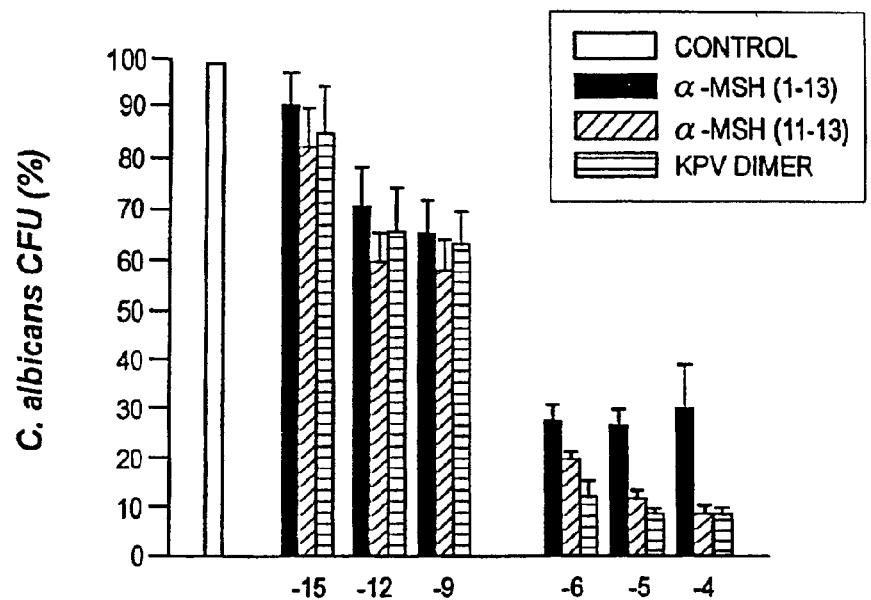
FIG. 1 illustrates the effect of α-MSH (1–13) and α-MSH (11–13) and the peptide VPK-Ac-CC-Ac-KPV on *C. albicans* colony forming units compared to controls. All three molecules significantly decreased *C. albicans* colony forming units over a broad range of peptide concentrations.

Furthermore, these modified analogs of α-MSH and/or its derivatives can also form dimers as exemplified by the KPV (SEQ ID NO:1) dimer in FIG. 1.

EXAMPLE II

Use of α-MSH and/or its Derivatives in Treatment of Pruritis

In a subject animal with a diagnosed and confirmed condition resulting in pruritis, a shampoo therapy can be prescribed. An examination by a veterinarian leads to a diagnosis of flea infestation with flea saliva reaction resulting in protopathic or epicritic pruritis. Examination reveals no secondary infection. Treatment can include a topical application via shampoo therapy of α-MSH and/or its derivatives carried in a shampoo of preferred texture and palliative properties. Treatment may be directed to twice a day shampooing or once a day shampooing followed by a rinse treatment incorporating Domeboro® or Aveeno® and αMSH and/or its derivatives. Treatment can be continued until the pruritis and/or infestation has been resolved.

EXAMPLE III

Use of α-MSH and/or its Derivatives in an Animal with Pruritis Resulting in Self-Excoriation and Secondary Infection An animal has epicritic pruritis of unknown etiology. This animal has been agitated by the pruritis to the degree of auto-mutilation. The open would from the excessive excoriation becomes secondarily infected with *Staphylococcus aureus* creating a potential cellulitic infection. After diagnosis, a veterinarian can debride the wound under local anesthesia. Following the debridement a dressing of α-MSH and/or its derivatives soaked gauze or other absorbent material may be employed.

As mentioned above, excoriation may create open lesions as well as those typically associated with the underlying pathology. These open lesions may be secondarily infected by opportunistic skin pathogens; *Staphylococcus Aureus, Pityrosporon* sp. or *Tricophyton rubrum,* for example. It is well known that steroid therapy has a tendency to "mask infection" by suppressing the host response to infection. Although the suppression of the inflammatory response is desirable for the reduction of pain, edema and erythema, the inflammatory response is integral to the host defense mechanism against infection. Steroids used alone may ameliorate the pruritis and the symptoms associated with inflammation but may allow an infection to go unnoticed and to become serious and, in systemic infection, be life threatening. α MSH (11–13), KPV (SEQ ID NO:1), has been shown to have both antibacterial and antifungal properties and therefore does not present the same risk of masking an infection.

EXAMPLE IV

Antifungal Properties Associated with α-MSH and/ or its Derivatives

Example IV suggests that α-MSH (11–13), α-MSH (6–13) and α-MSH (1–13) exhibit similar antifungal properties in general and similar anti-candidal properties specifically, as flucanazole over an exceedingly broad range of concentrations and therefore further suggests that α-MSH (11–13), α-MSH (6–13) and α-MSH (1–13) may be therapeutic in treating fungal-based animal pruritis or pruritis having a fungal component.

*C. albicans* ($1 \times 10^6$/ml in HBSS) was incubated in the presence or absence or α-MSH (1–13) or α-MSH (11–13) at concentrations in the range of $10^{-15}$ M to $10^{-6}$ M for 2 hours at 37° C. Cells were then washed in cold distilled water and diluted with HBSS to a concentration of 100 organisms/ml. One-ml aliquots were dispensed on blood agar plates and incubated for 48 hours at 37° C. Organism viability was estimated from the number of colonies formed.

In subsequent experiments using familiar procedures we compared activity of α-MSH (4–10), α-MSH (6–13), α-MSH (11–13), ACTH (1–39), (18–39) and fluconazole, the latter an established antifungal agent. Melanocortin peptides and fluconazole were tested in concentrations of $10^{-6}$ M to $10^{-4}$ M. There were at least six replicates for each concentration of peptide.

FIG. 1 shows that *C. albicans* colony forming units (CFU) were greatly reduced by α-MSH (1–13) and α-MSH (11–13). FIG. 1 also shows that the VPK-Ac-CC-Ac-KPV peptide also inhibited *C. albicans* colony formation. Concentrations of all three peptides from $10^{-12}$M to $10^{-4}$M had significant inhibitory effects on CFU ($p<0.01$ vs. control).

Figure 2:
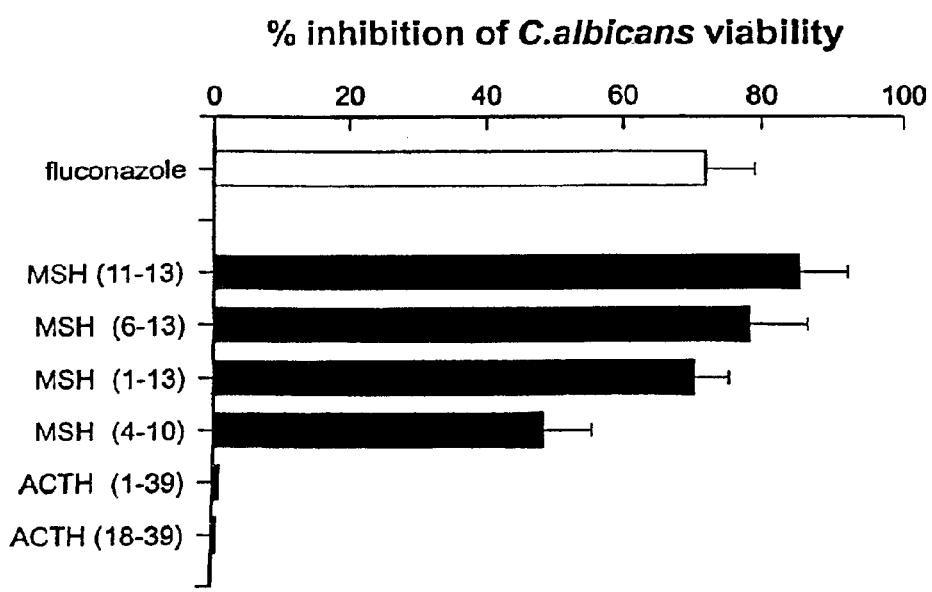
FIG. 2 represents a comparison of candidacidal activity of certain melanocortin peptides and fluconazole (all $10^{-6}$M).

FIG. 2 demonstrates that in experiments comparing the relative potency of $10^{-4}$M melanocortin peptides in reducing *C. albicans* viability, α-MSH (11–13), α-MSH(6–13) and α-MSH(1–13) were the most effective. Their inhibitory activity was similar to that of equimolar fluconazole. The core α-MSH sequence (4–10), which has behavioral effects but little anti-inflammatory activity, caused approximately 50% inhibition of CFU. FIG. 2 also shows that although this inhibitory effect was substantial ($p<0.01$ vs. control), it was significantly less than that caused by α-MSH fragments bearing the KPV signal sequence, i.e., α-MSH (6–13) and α-MSH (11–13) ($p<0.01$), or the parent molecule α-MSH (1–13)($p<0.05$). ACTH (1–39) and the ACTH fragment (18–39) did not reduce *C. albicans* viability. Even higher concentrations of these ACTH peptides (up to $10^{-4}$M) were likewise ineffective in reducing *C. albicans* CFU (results not shown in the figures).

These results show that α-MSH (1–13), its C-terminal tripeptide α-MSH (11–13), and other α-MSH fragments have significant fungicidal effects against *C. albicans.* The most effective of the α-MSH peptides were those including the C-terminal amino acid sequence KPV (SEQ ID NO:1) of the α-MHS sequence, i.e., α-MSH (1–13), α-MSH (6–13)

and α-MSH (11–13). In addition, the sequence VPK-Ac-CC-AC-KPV has also been shown to be at least as effective as α-MSH (11–13) against microbes. The α-MSH core sequence (4–10), which is known to influence learning and memory, but has little antipyretic and anti-inflammatory influence, was effective, but less so. The ACTH peptides (1–39) and (18–39) did not have significant candidacidal effects. These observations indicate that antifungal activity is not common to all melanocortin peptides, but rather is specific to α-MSH amino acid sequences, and most particularly to the C-terminal amino-acid sequences of α-MSH. This strongly suggests that α-MSH (1–13), its C-terminal tripeptide α-MSH (11–13), and other α-MSH fragments could serve as a basis for a therapeutic treatment for pruritis having a fungal component.

EXAMPLE V

Effects of α-MSH and/or its Derivatives on Candidal Germination

Example V demonstrates that α-MSH (1–13), α-MSH (6–13) or α-MSH (11–13) strongly inhibits candidal germination. Accordingly, Example V also suggests that α-MSH (1–13), α-MSH (6–13) or α-MSH (11–13) may be therapeutic in the treatment of aninal pruritis having a fungal component and specifically having a candidal component.

C. albicans from stationary phase cultures were washed twice with distilled water and suspended in HBSS to a final concentration of $2 \times 10^6$/ml. Hyphal growth was induced by addition of 10% inactivated horse serum (GIBCO/BRL, Great Britain) to yeast incubated for 45 minutes at 37° C. with continuous shaking. Horse serum was removed by washing cells twice with HBSS and incubation was continued for 60 minutes at 37° C. in the presence of α-MSH (1–13), α-MSH (6–13) or α-MSH (11–13) at a concentration of $10^{-6}$M with continuous shaking. The percentage of filamentous cells was evaluated under a light microscope with the aid of hemocytometer. Experiments were run in triplicate and at least 200 cells were scored. Photomicrographs were taken with an MC 100 camera attached to an Axioskop Zeiss microscope.

FIGS. 3A–D show that co-incubation of C. albicans with α-MSH (1–13) or α-MSH (11–13) inhibited germ tube formation induced by horse serum, α-MSH (1–13) caused 28–32% reduction in the number of filamentous cells; the tripeptide inhibited germination by 54–58%. The octapeptide α-MSH (6–13) had similar activity (approximately 50% inhibition) (not shown).

The pathogenesis of C. albicans infection involves adhesion of yeast cells to epithelial cells, commonly found in the membranes of the ears, eyes, nose and throat and/or endothelial cells, followed by morphologic switching of the yeast cells from the ellipsoid blastospore to various filamentous forms: germ tubes, pseudohyphae and hyphae. Gow, N. A., Germ Tube Growth of Candida Albicans, Curr. Topics Med. Mycol. 8, 43–45 (1997). The results also show that in addition to direct candicidal properties, α-MSH (1–13), its C-terminal tripeptide MSH (11–13), and other α-MSH fragments interfere with germination and adhesion of candida to the epithelium. This suggests that if the germination and adhesion of candida could be interfered with, animal pruritis having a fungal component could be treated with therapy based upon α-MSH (1–13), its C-terminal tripeptide α-MSH (11–13), and other α-MSH fragments.

EXAMPLE VI

Use of α-MSH and/or its Derivatives in Treatment of Candidias is do not Adversely Affect the Host Defense Mechanism Example VI illustrates that α-MSH and/or its derivatives exhibit their anti-fungal properties in general and anti-candidal properties specifically, without compromising the ability of human neutrophils to independently combat infection. Example VI further suggests that systemic or topical administration of α-MSH and/or its derivatives may be used to treat animal pruritis having a fungal component.

Venous blood (20 ml) from healthy volunteers was anticoagulated with heparin. Neutrophils were isolated using dextran sedimentation and Ficoll-Hypaque (Sigma Chemical Co., St. Louis, Mi., USA) centrifugation. Erythrocytes were lysed via hypotonic shock. Neutrophils represented at least 97% of the cell suspension. Cell viability, estimated by trypan blue exclusion, was >98%. Neutrophils were suspended to a final concentration in HBSS.

C. albicans ($1 \times 10^6$) were opsonized with human AB serum in a shaking water bath for 30 minutes at 37° C. Organisms were then incubated with neutrophils in medium or in medium with α-MSH (1–13) or α-MSH (11–13) in concentrations of $10^{-15}$ M to $10^{-4}$ M in a shaking water bath for 2 hours at 37° C. After incubation, the culture tubes were placed on ice to stop growth and extracellular organisms were washed twice with centrifugation at 1000×g at 4° C. A 2.5% sodium desoxycholoate solution was added to obtain a suspension of $10^6$ cells/ml. Two 1/100 serial dilutions in HBSS were made to obtain a final suspension of 100 cells/ml. Aliquots of 1 ml were dispensed on blood agar plates and incubated for 48 hours at 37° C. Colony forming units (CFUs) were counted at the end of the incubation period. Experiments were run in triplicate and repeated using blood from 5 different donors.

FIG. 4 shows that α-MSH (1–13) and α-MSH (11–13) enhanced the killing of C. albicans by human neutrophils when administered in concentrations of $10^{-12}$M to $10^{-4}$M ($p<0.01$). Therefore, enhanced killing occurred over a very broad range of concentrations including picomolar concentrations, i.e. the quantity of α-MSH found in human plasma. Catania, A., Airaghi, L., Garofalo, L., Cutuli, M., Lipton, J. M., *The Neuropeptide α-MSH in AIDS and Other Conditions in Humans*, Ann. N.Y. Acad. Sci. 840, 848–856 (1998).

Reduced killing of pathogens is a dire consequence of therapy with corticosteroids and possibly nonsteroidal anti-inflammatory drugs during infection. Stevens, D. L., *Could Nonsteroidal Anti-inflammatory Drugs (NSAIDS) Enhance Progression of Bacterial Infections to Toxic Shock Syndrome?*, Clin. Infect. Dis., 21, 977–80 (1997); Capsoni, F., Meroni, P. L., Zocchi, M. R., Plebani, A. M., Vezio, M., *Effect of Corticosteroids on Neutrophil Function: Inhibition of Antibody-dependent Cell-mediated Cytotoxicity (ADCC)*, J. Immunopharmacol. 5, 217–230 (1983). This effect is particularly dangerous in immunocompromised patients.

These results also suggest that α-MSH (1–13), its C-terminal tripeptide α-MSH (11–13), and other α-MSH fragments would be useful for treatment of animal pruritis without compromising the immune system.

EXAMPLE VII

Anti-Inflammatory Quality of α-MSH and/or its Derivatives

Example VII suggests that systemic or topically administered α-MSH may be useful in reducing the inflanimation associated with animal pruritis. Example VII further suggests that such applications of α-MSH would be clinically therapeutic for the treatment of animal sinusitis, commonly associated with allergic pruritis. The anti-inflammatory activity of the tripeptide α-MSH (11–13), KPV (SEQ ID NO:1), was demonstrated through the use of an animal model developed by Sparrow and Wilhelm (1957), J. Physiol., 137:51–65. This model relies on the principal that localized, subcutaneous injections of histamine will result in a localized increase in capillary permeability. When the test animal has been pretreated with blue dye intravenously, the localized histamine injections will elicit blue-colored wheals around the injection site. Thus, by pre-administration of an effective anti-inflammatory agent the blue color of the histamine-induced wheals will be much less pronounced, with the amount of color reduction being dependent on the relative amount and/or potency of the anti-inflammatory agent used.

Non-molting New Zealand white rabbits were used for the Sparrow/Wilhelm assay. The skin of the rabbits back was closely clipped 1–2 days previous to the experiment, but not depilated, and the rabbits were kept warm until tested. Various amounts of the protected tripeptide Ac-Lys-Pro-Val-$NH_2$ were injected intravenously into an ear vein approximately 15 minutes prior to intravenous injection of blue dye. Control rabbits received sham injections. Fifteen minutes following injection of the agent or sham, the rabbits received approximately 30 mg/kg of Pontamine blue dye as a 2.5% solution in 0.45% saline, into an exposed vein. Immediately following dye injections, histamine was injected intradermally in a 0.10 ml volume (1.25 mg histamine 0.1 ml volume) at several sites on each side of the spine. In all, one vertical row of six injections were made on each side of the spine. The relative intensity of the resultant blue wheals were scored by an independent observer 30 minutes after histamine injection. The results are displayed in Table I below.

TABLE I

Anti-inflammatory Activity of the Tripeptide

| No Animals Tested | Tripeptide Dose + | Result |
|---|---|---|
| 3 (2E, 1C)* | 5 | E lighter than C |
| 2 (1E, 1C) | 10 | E lighter than C |
| 2 (1E, 1C) | 5 | E lighter than C |
| 2 (1E, 1C) | 1.25 | E lighter than C |
| 2 (1E, 1C) | 0.625 | No difference observed |

*E = experimental; C control
+ Dosages in ug of protected tripeptide per kg body weight, administered intravenously.

As will be appreciated from the results displayed in Table I, intravenous doses down to 1.25 ug tripeptide per kg body weight resulted in an appreciable reduction in histamine-induced blue weal formation and is thus indicative of an effective anti-inflammatory action. At doses of 5 and 10 ug/kg, the observed response was even more pronounced. Also as will be appreciated, the anti-inflammatory effect of the tripeptide is observed at relatively lower doses as compared to its anti-pyretic effect.

EXAMPLE VIII

Comparison of α-MSH and/or its Derivatives with a Glucocorticoid

Example VIII still further suggests that the anti-inflammatory properties of α-MSH and/or its derivatives may be clinically therapeutic for the treatment of pruritis and may serve as substitute for glucocorticoid based treatment regimens. A second in vivo bioassay for anti-inflammatory activity was conducted in which the action of the tripeptide was compared to that of hydrocortisone. In this assay, the two agents were given at similar doses and tested for their independent ability to inhibit carrageenan-induced swelling in rat paws. This assay, the rat paw edema test, was conducted generally as it is typically performed in the art, for example, as described by Winter et al. (1962), Proc. Soc. Exp. Biol. Med., 111:544 or in U.S. Pat. No. 4,150,137.

Briefly, the assay was performed as follows. Each of twenty-four male Sprague-Dawley rats was assigned to one of four groups: Tripeptide treatment and controls (matched according to body weight and initial paw volume), hydrocortisone treatment and matched controls. The volume of the right rear paw of the test and control animals was determined using standard procedures and a mercury displacement volumetric technique. An intraperitoneal injection of the tripeptide (Ac-Lys-Pro-Val-$NH_2$, 100 mg/kg, N=6), of hydrocortisone (100 mg/kg, N=6), or saline (matched volume, N=12) was given to each rat. One hour later 0.5 ml of 1% lambda carrageenan in saline solution was injected into the right rear paw of the animals and the paw volume was again recorded (baseline measure). For comparison of the effects of the two treatments, paw volume of experimental animals measured at hourly intervals was expressed as a percentage of the volume change of their respective matched controls.

The results of this experiment are shown in FIG. 7. As will be appreciated from this data, except for the first hour when hydrocortisone markedly inhibited swelling ($p<0.05$, Mann-Whitney test), there was no significant difference in the inhibition of paw edema caused by the tripeptide and hydrocortisone ($p<0.20$). These results indicated that the tripeptide inhibits inflammation as well as the classic anti-inflammatory agent, when given in an equal dose by weight, albeit with a slightly different time course. Based on the present results and the known effects of hydrocortisone and inflammation, it may be concluded that the tripeptide Lys-Pro-Val (SEQ ID NO:1) can be used to reduce inflammation associated with pruritis.

EXAMPLE IX

Alteration of Tripeptide Chirality Effects the Anti-inflammatory Ability of α-MSH and/or its Derivatives Example IX suggests that α-MSH and its derivatives may be employed in general to reduce inflammation and in particular may be employed to reduce inflammation associated with pruritis. Hiltz, M. E., Catania, A., Lipton, J. M., Anti-Inflammatory Activity of α-MSH (11–13) Analogs: Influence of Alteration in Stereochemistry, 12 Peptides 767 (1981). More particularly, Example IX suggests that the C-terminal tripeptide of α-MSH and/or its derivatives has potent anti-inflammatory properties and further suggests that alterations in amino acid chirality of the tripeptide α-MSH (11–13), KPV, can markedly affect the peptides anti-inflammatory properties.

Female BALB/C mice (Simonsen Laboratories), 7 weeks old, were housed at 23–25° C. in groups of no more than 5 per cage [28 cm (L)×18 cm (W)×13 cm (H)]. They were allowed to acclimatize to standard lighting and temperature conditions for at least 1 week, with food and water available ad lib, before the experiment began. Five to ten animals were randomly assigned to each treatment group each test day, and all experiments were repeated at least twice to confirm reproducibility. To reduce error due to slight differences in responses to the irritant of animals from different shipments, tests of each agent were performed as separate experiments in which experimental and control animals were drawn from the same shipment.

In the experiments each animal was anesthetized with 1 mg of pentobarbital sodium solution (50 mg/kg, Nembutal, Abbott Laboratories, Abbott park, Ill.). Baseline ear thickness was measured for both ears with a spring-loaded micrometer (Swiss Precision Instruments, Los Angeles, Calif.). Ear thickness was expressed in units of $10^{-3}$ cm; the average thickness of unstimulated ears was approximately $25–30 \times 10^{-3}$ cm. After baseline measurements were taken, one of six solutions was injected IP. Control animals received 0.2 ml of sterile saline, and experimental animals received Ac-α-MSH (11–13)-NH$_2$, i.e., Ac-Lys-Pro-Val-NH$_2$), Ac[D-Lys$^{11}$]α-MSH (11–13)-NH$_2$, Ac[D-Pro$^{12}$]α-MSH (11–13)-NH$_2$, Ac[D-Val$^{13}$]α-MSH (11–13)-NH$_2$ or Ac-[D- Lys$^{11}$, D-Val$^{13}$]α-MSH (11–13)-NH$_2$ in the same volume of saline. All of the peptides were custom synthesized by Peninsula Laboratories (Belmont, Calif.) and were determined to be both pure by HPLC and to possess the expected amino acid analytical composition. The doses of the tripeptides were 10 μg ($2.6 \times 10^{-8}$ M), 20 μg ($5.2 \times 10^{-8}$ M), 40 μg ($1.04 \times 10^{-7}$ M), and 80 μg ($2.08 \times 10^{-7}$ M). Immediately after saline or α-MSH injection, a micropipette was used to coat both sides of each ear with 10 μl (40 μl per mouse) of a 0.5% picryl chloride (Polysciences, Warrington, Pa.) solution in acetone.

Ear thickness was remeasured 3 and 6 h after picryl chloride application. Swelling was determined by subtracting baseline thickness from the measurements for each ear at 3 and 6 h. The differences for both ears were then averaged for the final analysis. On rare occasions when swelling did not occur in the control animals, the data for that day were considered invalid and were not used in the final analysis.

Repeated-measure ANOVA techniques were used to determine if there was an overall difference among group data for each peptide tested in separate experiments. In those cases in which the ANOVA yielded significant results, Dunnett's test was then used to compare the effects of peptide doses with control (saline) data for each of the two time periods, 3 and 6 h.

FIG. 8 illustrates inhibition by α-MSH (11–13) of inflammation induced in the ear of a mouse induced by picryl chloride application. Ac-α-MSH (11–13)-NH$_2$ inhibited acute inflammation. The ANOVA showed a highly significant dose effect, $F(4,92)=9.35, p<0.0001$. There was also a significant time effect, $F(1,92)=40.8, p<0.001$, but no significant interaction. The average swelling in the controls was significantly greater than in any of the peptide treatment groups at both 3 and 6 h ($p<0.05$, Dunnett's test, two-tail).

FIG. 9 illustrates that Ac[D-Lys$^{11}$]α-MSH (11–13)-NH$_2$ likewise significantly reduced inflammation [$F(4,135)=7.83$ $p<0.0001$] in the ear of a mouse induced by picryl chloride application. Ear swelling after all doses of peptide was less than control ($p<0.05$). There was a significant time effect, $F(1,135)=43.8, p<0.001$, but no significant dose-time interaction. FIG. 10 illustrates that Ac[D-Pro$^{12}$]α-MSH (11–13)-NH$_2$ had no significant effect on inflammation [$F(4,139)= 0.62, p>0.65$]. By contrast, FIG. 11 illustrates that Ac[D-Val$^{13}$]α-MSH (11–13)-NH$_2$ had a marked inhibitory influence [$F(4,136)=19.6 \ p<0.001$]. There was a significant time effect in the Ac[D-Val$^{13}$] experiment, $F(4,138)=3.96$, $p<0.005$, likely due to increases over time for the control, 10 and 80 μg groups and little change for the 20 and 40 μg groups. Dunneff's test applied to control and treatment data for the 3- and 6-h time periods indicated that the control swelling was significantly greater than in the peptide treatment groups ($p<0.01$).

As FIG. 12 illustrates, Ac-[D- Lys$^{11}$, D-Val$^{13}$]α-MSH (11–13)-NH$_2$ showed a significant overall reduction in inflammation [$F(4,102)=19.8, p<0.0001$], and a significant time effect, $F(1,102=73.2 \ p<0.0001$, but no significant interaction. Treatment means were all significantly less ($p<0.01$) than control values for both the 3- and 6 h measurements.

As is shown in Table 2, the results of the experiments were converted to percent inhibition of swelling for comparisons of the effectiveness of the peptide conformations. The two peptides with D-Val$^{13}$ conformation induced greater and more consistent anti-inflammatory effects at 3 and 6 h than did the other tripeptides. Although in these experiments, the well-known bell-shaped influence of peptides complicated the comparisons, the D-Val$^{13}$ tripeptides were generally more potent and their effects were sustained in the 6 h measurement. D-Lys$^{11}$ substitution did not increase the potency or duration of anti-inflammatory activity and the strong action of the largest does of Ac-α-MSH (11–13)-NH$_2$ suggests that its actions rank roughly third among those recorded. The lack of significant effect on inflammation of the Ac[D-Pro$^{12}$]α-MSH (11–13)-NH$_2$ indicates that the L-Pro configuration is likely central to the anti-inflammatory activities of the molecule.

Altering the stereochemical make-up of the tripeptide via D-substitution had two major effects: increased potency in the case of Ac[D-Val$^{13}$]α-MSH (11–13)- NH$_2$ and Ac-[D-Lys$^{11}$, D-Val$^{13}$]α-MSH (11–13)-NH$_2$ reduced the anti-inflammatory activity in Ac[D-Pro$^{12}$]α-MSH (11–13)-NH$_2$.

These results suggest that the C-terminal tripeptide of α-MSH and/or its derivatives has potent anti-inflammatory properties and further suggest that alterations in amino acid chirality tripeptide can markedly affect the peptides α-MSH anti-inflammatory properties.

EXAMPLE X

The Anti-inflammatory Action of α-MSH and/or its Derivatives is Achieved Through Both Centrally and Peripherally Mediated Mechanisms Example X suggests that α-MSH and/or its derivatives reduces inflammation via centrally and peripherally mediated mechanisms and accordingly, systemic or topical administration of α-MSH and/or its derivatives may be therapeutically effective in the treatment of veterinary pruritis. See Macaluso, A., McCoy, D., Ceriani, G., Watanabe, T., Biltz, J., Catania, A., and Lipton, J. M., *Anti-inflammatory Influences of α-MSH Molecules: Central Neurogenic and Peripheral Actions*, 14(4), J. of Neuroscience 2377–2382 (1994).

Female BALB/c mice (Simonsen Laboratories, Gilroy, Calif.), 7–8 weeks old, were housed at 23–25° C. in groups not exceeding five animals per cage [28 cm (L)×18 cm (W)×13 cm (H)]. Before the experiments they were acclimatized for not less than 1 week before experimentation to standard lighting and temperature conditions with food and water freely available.

Mice were anesthetized with 10% pentobarbital sodium solution (1 mg/mouse, 50 mg/ml, Nembutal sodium solution; Abbott Laboratories, North Chicago, Ill.). Baseline ear thickness measurements were taken with a spring-loaded micrometer (Swiss Precision Instruments, Los Angeles, Calif.). Ear thickness was expressed in cubic centimeters and was measured at least twice at each time point. The average thickness of unstimulated ears was 26.82 cm$^{-3}$. Inflammation was induced by intradermal injection of 20 µl of recombinant human IL-1β (1500 U; Genzyme, Cambridge, Mass.) in one ear of each mouse using a 28 gauge needle (Hiltz et al., 1992). Measures of ear thickness were repeated 4 and 6 hr later, while the mice were under sodium pentobarbital anesthesia. Edema was assessed by subtracting baseline measures from 4 and 6 hr readings for each animal. α-MSH (11–13) (1663.9 gm/mol; Peninsula Laboratories, Belmont, Calif.) or α-MSH (11–13) (383.48 gm/mol; Peninsula Laboratories) dissolved in saline was injected intracerebroventricularly (20 µl) using procedures described previously (Lipton et al., 1991; Lipton and Catania, 1993).

Several agents were administered at the time of ear challenge to pharmacologically block certain receptors: atropine (Sigma Chemical Co.; 150 µg i.p.), a muscarinic receptor blocker that acts on autonomic end-organ receptors, was chosen because of links between inflammation and modulation of pain and the finding that muscarinic antagonists increase pain threshold (Hartvig et al., 1989); phentolamine (Sigma; 150 µg i.p.) an agent that competes for occupancy of α-adrenergic receptors; propranolol (Sigma; 150 µg, i.p.; 30 µg, i.c.v.), a nonspecific competitive antagonist for β-adrenergic receptors. After positive effects were observed with propranolol, selective antagonists of β-adrenergic receptors were tested; atenolol (Sigma; 150 µg, i.p.), a β$_1$-adrenergic receptor antagonist; butoxamine (Sigma; 150 µg, i.p.), a β$_2$-adrenergic receptor blocker.

Because surgical dissection of trigeminal structures that innervate the ear of the mouse is very difficult, tests to learn whether descending neural pathways are essential to the anti-inflammatory activity of centrally administered α-MSH peptides were performed in mice with inflammation induced in a hind paw. In these experiments, each animal was anesthetized with pentobarbital sodium solution as above. Baseline footpad thickness of both hind paws was measured with a spring-loaded micrometer (Swiss Precision Instruments, Los Angeles, Calif.). Paw thickness was expressed in units of 10$^{-3}$ cm; average thickness of unstimulated paws was 171.5×10$^{-3}$ cm across shipments of animals. Kappa carrageenan (Sigma) dissolved in saline (0.05%, 20 µl) was injected (28 gauge allergy test syringe) into one footpad, and saline (20 µl) was injected into the other. For the analyses, the increase in thickness of the control saline-injected paw of each animal was subtracted from that of the carrageenan-injected paw, to eliminate the influence of mechanical injury and volume of the injected fluid. To be certain that mice with severed spinal cords can react to anti-inflammatory agents, prednisolone (2.5 mg/mouse (IP injection)) was administered to 10 mice with spinal transection and inflammation induced by carrageenan. Treatment with the locally acting steroid reduced swelling up to 29% (average, relative to saline controls) at 4.5 h. after carrageenan. This finding indicates that spinal transection in these mice does not result in stasis of inflammation that is unalterable as a result of vasodilation, hypotension, or other hemodynamic changes.

Pilot studies indicated that interruption of the spinal cord of the mouse by surgical exposure, visualization, and severing with a scalpel blade resulted in marked bleeding, morbidity, and death in a substantial number of animals. However, a standardized crushing of lumbar vertebrae with a hemostat was effective in severing the cord; no deaths were caused by this treatment. In the experiments proper, all animals were tested after cord section when the anesthesia had worn off: none showed behavioral or motor responses to pinching of the hind feet with a hemostat; all had complete paralysis of the hind limbs. Data of animals that did not meet these criteria were excluded from the analyses. The experiments were limited to 4.5 h to reduce problems of bowel and bladder dysfunction. Immediately after the 4.5 h measurements all mice were killed with an overdose of sodium pentobarbital.

Because of the size of the experiments and the requirement for several shipments of animals over time, several experiments were performed, each with complete treatment and control groups drawn from the same shipment of mice. Omnibus analysis of variance techniques (Dynastat, Washington, D.C.) were used to test overall differences among group means. Tukey's protected t test was used to compare individual means. Probability values of <0.05 were considered significant.

In order to determine whether α-MSH and/or its derivatives anti-inflammatory properties are centrally or peripherally mediated, propranolol, a β-receptor blocker, was administered centrally and peripherally. As is shown in FIG. 13, when propranolol was injected centrally there was little effect on the anti-inflammatory influence of α-MSH (1–13) (inhibition by α-MSH was 36% and 32% at 4 hr and 6 hr respectively). By contrast when 300 µg of propranolol was administered intraperitoneally, the anti-inflammatory response of α-MSH was inhibited. This indicates that competitive binding of peripheral β-receptors inhibits the anti-inflammatory influence of centrally administered α-MSH. In subsequent tests to determine the role of which β-adrenergic receptors were connected with the anti-inflammatory effect of centrally administered α-MSH. As is shown in FIG. 14, when atenolol, a β$_1$ adrenergic antagonist was injected IP, there was little inhibition of α-MSH (1–13)'s anti-inflammatory activity. By contrast, when the β$_2$-receptor antagonist, butoxamine, was similarly administered, the α-MSH (1–13)'s anti-inflammatory effects were significantly reduced. These results indicate that β$_2$-receptor activity in the periphery is essential to the anti-inflammatory action of α-MSH and/or its derivatives. As is shown in FIG. 15, blockade of α-adrenergic receptors with phentolamine, and cholinergic (muscarinic) receptors with atropine, did not alter the anti-inflammatory effect of α-MSH (1–13).

As shown in FIG. 16, central administration of α-MSH (1–13) in spinal cord intact mice markedly inhibited inflammation induced in the hind paw. The greatest effect was at 3 h (57% inhibition); inhibition was less at 4.5 h (29%). By contrast, spinal cord transection significantly reduced the anti-inflammatory effect of centrally administered α-MSH (1–13). As is shown in FIG. 17, although transection of the spinal cord significantly reduced the early anti-inflammatory effect of α-MSH (1–13) given intraperitoneally, there was a significant, although smaller, inhibitory effect later in the period.

To determine if the influence of systemically administered α-MSH requires it to act on the brain to induce descending inhibitory signals, α-MSH (1–13) was administered IP to mice with spinal cord transection. FIG. 18 suggests that the tripeptide had a marked inhibitory effect on inflammation. These findings suggest that the anti-inflammatory, effects of α-MSH (1–13) do not require descending inhibitory signals from the brain. These findings suggest that the anti-inflammatory effects of α-MSH (1–13) and/or its derivatives are a completely generalized function without regard to a specific tissue system, involving both central nervous system components and periphery β-receptor instructions. This further suggests that topical or systemic administration of α-MSH (1–13) and/or derivatives would be broadly effective at treating inflammation in general and the inflammation associated with pruritis specifically.

EXAMPLE XI

α-MSH and/or its Derivatives Reduces Cytokine Mediated Inflammation

Example XI suggests that the anti-inflammatory peptides of α-MSH and/or its derivatives may be associated with reducing the cytokines connected to the inflammatory response including IL-6 and TNF-α and NO. See Delgado, R., Carlin, A., Alraghi, L., Demitri, M., Meda, L., Galimberti, D., Pierluigi, B., Lipton, J. M., Catania, A., *Melanocortin Peptides Inhibit Production of Proinflammatory Cytokines and Nitric Oxide by Activated Microglia*, 63 J. of Leukocyte Biol. 740 (1998). This further suggests the α-MSH and/or its derivatives may be the therapeutically effective, when administered topically or systemically for the treatment of pruritis.

The N9 clone of murine microglial cells was obtained by immortalization of embryonic brain cultures with the 3RV retrovirus carrying an activated v-myconcogene. N9 cells were cultured in T-75-cm$^2$ culture flasks (Corning, Cambridge, Mass.) and maintained at 37° C. in a humidified incubator under 5% $CO_2$ atmosphere in RPMI 1640 supplemented with 2 mM L-glutamine, 50 U/mL penicillin G, 50 μg/mL streptomycin sulfate (GIBCO-BBL, Paisley, UK), and 10% heat-inactivated fetal bovine serum (FBS, Hyclone Lab, Inc., Logan, Utah) until experiments were performed. Cells were used between the first and the tenth passage.

Sub-confluent microglial cells were washed twice with phosphate-buffered saline (PBS) and incubated with trypsin 0.025% and ethylenediaminetetraacetate (EDTA) 0.02% without calcium and magnesium for 3 min. at 37° C. to detach the cells from the culture flask. Cells were then resuspended in medium and incubated in 24-well tissue-culture plates at a concentration of 2×10$^5$ cells/mL for 16 h in a humidified incubator (37° C., 5% $CO_2$). Growth medium was removed and cell monolayers were stimulated with 10 ng/mL lipopolysaccharide (LPS, from *Escherichia coli* 055:B5, Sigma Chemical Co., St. Louis, Mo.) plus 1 U/ml, murine IFN-γ (Sigma). To test effects of melanocortin peptides, concentrations (1, 10, 25, 50 and 100 μM) of α-MSH (1–13), α-MSH (11–13), and ACTH (1–24) (Sigma) were dissolved in medium and added to wells 10 min before treatment with LPS+IFN-γ. Although production of TNF-α and NO was reduced to even much lower concentrations of the peptides, concentrations in the micromolar range had the most profound and consistent inhibitory effects. Although lower concentrations were more effective in previous research, we elected to use micromolar concentrations in the present studies because they were more effective for the experimental conditions (cell type, incubation period, concentration of the stimuli). Cell-free supernatants were harvested after 24 h incubation and assayed for TNF-α, IL-6 and $NO_2$. Viability of cells was assessed by trypan blue exclusion for each experimental condition; it was consistently >98%. Dexamethasone (Sigma) and N-monomethyl-L-arginine (L-NMMA) 100 μM, Cayman Chemical, Ann Arbor, Mich.) were used as positive controls for TNF-α and NO inhibition, respectively. Tests were repeated in at least three independent experiments and assays were performed in triplicate.

TNF-α bioactivity was measured in supernatants of cell cultures by standard cytotoxicity assay using L929 cells and recombinant human TNF-α (Sigma) as standard. The detection limit of the bioassay was 20 pg/mL. IL-6 was measured using a commercial murine enzyme-linked immunosorbent assay (ELISA: RPN 2714, Amersham, Little Chalfont, UK).

NO is rapidly oxidized to nitrite ($NO_2$) in culture medium, and nitrite concentration is an indicator of NO production. Cell-free culture supernatants were mixed with equal amounts of Griess reagent (1% sulfanilamide, 0.1% napthylethylenediamide in 2.5% phosphoric acid) in wells of 96-well ELISA plates. Samples were incubated at room temperature for 10 min and absorbency was measured at 540 nm with the use of a microplate reader. Nitrite concentrations were calculated using a sodium nitrite standard curve.

cAMP accumulation in N9 cells was measured as previously described. Briefly, cells in six-well plates were co-incubated at 37° C. with (1) medium; (2) forskolin (100 μM); (3) LPS (10 ng/mL)+IFN-γ (1 U/mL); (4) α-MSH (1–13) or α-MSH (11–13) (1, 10, 50 μM); (5) LPS+IFN-γ and either α-MSN (1–13) or α-MSH (11–13) (10 μM). Reactions were stopped after 3 min by aspirating supernatants, immediately adding 1 mL ethanol at −20° C. and freezing. cAMP content in the ethanol-soluble fraction was measured using an enzyme immunoassay kit (Amersham).

Total cellular RNA was extracted from 10$^6$ adherent microglial cells plated in six-well tissue culture plates (Corning). Electrophoresis of RNA samples (10 μg/lane) was performed in 1% agarose/2.2 M formaldehyde gels and the gels subsequently blotted onto nylon filters by capillary action and baked for 2 h before prehybridization. The cDNA fragments encoding murine TNF-α and mouse macrophage iNOS were $^{32}$P-labeled using the Ready-To-Go DNA Labeling Kit (Pharmacia, Uppsala, Sweden) before hybridization of nylon filters and autoradiography. Blots were subsequently rehybridized with human glyceraldehyde-3-phosphate dehydrogenase (G-3-PDH) cDNA probe as an internal control (Clontech Laboratories, Inc., Palo Alto, Calif.).

Microglia were plated in 24-well plates at a concentration of 2×10$^5$ cells/ml and α-MSH production was determined in cell-free supernatants after 24 h incubation with LPS, 10 ng/mL; IFN-γ, 1 U/mL; and LPS 10 ng/ml+IFN-γ, 1 U/mL, α-MSH was measured with a double antibody radioimmunoassay (Euro-Diagnostica AB, Malmo, Sweden). The sensitivity of the assay is 0.5 pg/mL and cross-reactivity with other POMC peptides (ACTH (1–24), ACTH (1–39), β-MSH, γ-MSH) is <0.002%.

Microglia as above in RPMI 1640 medium supplemented with 10% FBS were pre-incubated overnight with rabbit anti-α-MSH produced by resting microglia during the overnight adherence period. After preincubation, the medium was removed and cells co-incubated with LPS 10 ng/mL, IFN-γ 1 U/mL or LPS+IFN-γ diluted in 1 mL RPMI 1640 medium (10% FBS) containing the same rabbit anti-α-MSH antibody concentration used during pre-incubation. The cell-free supernatants were removed after a 24 h incubation and assayed for TNF-α, IL-6, and nitrite. Control samples were treated with rabbit IgG at the same dilution.

Effects of melanocortin peptides on cytokine and NO production were evaluated by repeated measures analysis of variance followed by Dunnet's test for specific comparisons. Probability values less than 0.05 were considered significant.

As is shown in FIG. 19 micromolar concentrations of α-MSH (1–13) significantly reduced IL-6 and $NO_2^-$ levels in microglia stimulated with LPS+IFN-γ for 24 hr. More particularly, α-MSH (1–13) reduced the production of TNF-α, IL-6 and $NO_2^-$ by 43, 31 and 42% respectively. FIG. 20 shows that α-MSH (11–13) reduced the production of TNF-α, IL-6 and $NO_2^-$ by 45, 50 & 40% respectively. FIG. 21 shows that ACTH (1–24) reduced the production of TNF-α, IL-6 and $NO_2$ in microglia by 38, 65 and 41% respectively. FIGS. 22 and 23 shows that incubation of microglia with α-MSH (1–13) and α-MSH (11–13) increased cAMP accumulation in resting cells and cells incubated with LPS+IFN-γ. FIG. 23 shows further that the magnitude of cAMP accumulation induced by α-MSH peptides was comparable to that caused by forskolin.

As shown in FIG. 24, Northern blot analysis suggests that the inhibitory influence of melanocortin peptides α-MSH (1–13), α-MSH (11–13) ACTH (1–24), on TNF-α and $NO_2$ release was likely caused by the inhibition of mRNA transaction for TNF-α and iNOS.

These results suggest that the melanocortin peptides α-MSH (1–13), α-MSH (11–13) and ACTH (1–24) all act on activated microglia to inhibit production of proinflammatory mediators TNF-α, IL-6 and NO. Because microglia stimulated with LPS and IFN-γ also secreted α-MSH, an autocrine anti-inflammatory circuit based on this potent peptide probably occurs in brain phagocytes, much as in peripheral monocytes. This idea is supported by the observation that immunoneutralization of endogenous α-MSH enhances production of proinflammatory mediators by activated microglia. Example XI therefore suggests that the mechanism of the anti-inflammatory peptides is agnostic to the location cause of the inflammation. Accordingly, Example XI further suggests that systemic or topical application of α-MSH and/or its derivatives may be therapeutic for the treatment of animal pruritis.

The preceding examples demonstrate the application of α-MSH and/or its derivatives for uses in both treatment of animal pruritis as well as suggesting different combination therapies. Further, specific examples of comparisons with traditional treatments and laboratory studies are provided. These are only examples and are not intended to limit the invention to these examples. It is understood that modifying the examples above does not depart from the spirit of the invention. It is further understood that the examples can be applied on their own or in combination with each other.

TABLE 2

| | % Inhibition | | Amino Acid | |
|---|---|---|---|---|
| | 3 h | 6 h | Analysis | % Purity |
| Ac-α-MSH(11–13)-$NH_2$ | | | K (0.99), P (1.01), V (0.94) | >99 |
| 10 μg | 26 | 25 | | |
| 20 μg | 21 | 19 | | |
| 40 μg | 33 | 26 | | |
| 80 μg | 50 | 42 | | |
| Ac-[D-Lys$^{11}$]α-MSH(11–13)-$NH_2$ | | | K (0.97), P (1.03), V(0.94) | >93 |
| 10 μg | 23 | 17 | | |
| 20 μg | 25 | 16 | | |
| 40 μg | 35 | 37 | | |
| 80 μg | 34 | 29 | | |
| Ac-[D-Pro$^{13}$]α-MSH(11–13)-$NH_2$ | | | K (0.99), P (1.01), V (0.97) | >93 |
| 10 μg | 4 | 8 | | |
| 20 μg | 11 | 5 | | |
| 40 μg | 10 | 8 | | |
| 80 μg | 8 | 6 | | |
| Ac-[D-Pro$^{13}$]α-MSH(11–13)-$NH_2$ | | | K (0.99), P (1.01), V (0.97) | >96 |
| 10 μg | 24 | 23 | | |
| 20 μg | 48 | 54 | | |
| 40 μg | 39 | 45 | | |
| 80 μg | 41 | 29 | | |
| Ac-[D-Lys$^{11}$, D-Val$^{13}$]α-MSH(11–13)-$NH_2$ | | | K (1.04), P (0.91), V (1.05) | >99 |
| 10 μg | 22 | 22 | | |
| 20 μg | 55 | 46 | | |
| 40 μg | 42 | 41 | | |
| 80 μg | 40 | 44 | | |

What is claimed is:

1. A veterinary composition for the treatment of animal pruritus comprising:
   (a) a therapeutically effective amount of polypeptide having a C-terminus sequence of KPV; and
   (b) a shampoo.

2. The veterinary composition of claim 1 wherein the polypeptide is selected from a group consisting of KPV (SEQ ID NO: 1), VPK-Ac-CC-Ac-KPV (SEQ ID NO: 5), HFRWGKPV (SEQ ID NO: 3), and SYSMEHFRWGKPV (SEQ ID NO: 4).

3. The veterinary composition of claim 1 wherein the shampoo is selected from the group consisting of clear liquid, liquid cream, solid cream, oil, and powder shampoos.

4. The composition of claim 1 wherein the polypeptide is (SEQ ID NO: 1).

5. The composition of claim 1 wherein the polypeptide is (SEQ ID NO 5).

6. The composition of claim 1 wherein the polypeptide is (SEQ ID NO 3).

7. The composition of claim 1 wherein the polypeptide is (SEQ ID NO 4).

8. A veterinary composition for the treatment of animal pruritus comprising:
   (a) a therapeutically effective amount of a polypeptide having a C-terminus sequence of KPV (SEQ ID NO: 1) selected from a group consisting of KPV (SEQ ID NO: 1), VPK-Ac-CC-Ac-KPV (SEQ ID NO: 5), HFRWGKPV (SEQ ID NO: 3), and SYSMEHFRWGKPV (SEQ ID NO: 4); and
   (b) a shampoo.

* * * * *

SEQUENCE LISTING

<160> NUMBER OF SEQ ID NOS: 4

<210> SEQ ID NO 1
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 1

Lys Pro Val
1

<210> SEQ ID NO 2
<211> LENGTH: 10
<212> TYPE: PRT
<213> ORGANISM: Artificial Sequence

```
<220> FEATURE:
<223> OTHER INFORMATION: Designed polypeptide with anti-inflammatory,
      anti-bacterial, anti-fungal and antipyretic properties.

<400> SEQUENCE: 2

Met Glu His Phe Arg Trp Gly Lys Pro Val
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 3

His Phe Arg Trp Gly Lys Pro Val
1               5

<210> SEQ ID NO 4
<211> LENGTH: 13
<212> TYPE: PRT
<213> ORGANISM: Homo sapiens

<400> SEQUENCE: 4

Ser Tyr Ser Met Glu His Phe Arg Trp Gly Lys Pro Val
1               5                   10
```